United States Patent [19]

Bradfield et al.

[11] Patent Number: 4,710,712

[45] Date of Patent: * Dec. 1, 1987

[54] METHOD AND APPARATUS FOR MEASURING DEFECTS IN FERROMAGNETIC ELEMENTS

[75] Inventors: James E. Bradfield; John E. Kahil; Mark S. Jaynes; Gordon L. Moake; Marvin Milewits; Curtis W. Bolton, III; Clive C. Lam; Roderic K. Stanley, all of Houston, Tex.

[73] Assignee: PA Incorporated, Houston, Tex.

[*] Notice: The portion of the term of this patent subsequent to Jan. 8, 2002 has been disclaimed.

[21] Appl. No.: 599,053

[22] Filed: Apr. 11, 1984

[51] Int. Cl.$^4$ .................. G01N 27/72; G01N 27/82; G01R 33/12

[52] U.S. Cl. .................. 324/227; 324/232; 324/233; 324/242

[58] Field of Search .......... 324/225, 226, 227, 232, 324/239–243, 262, 233

[56] References Cited

U.S. PATENT DOCUMENTS

| | | | |
|---|---|---|---|
| 2,467,306 | 4/1949 | Habig | 324/242 |
| 2,527,000 | 10/1950 | Drake | 324/218 |
| 2,560,845 | 2/1971 | Goldberg | 324/243 |
| 2,882,488 | 4/1959 | Price | 324/225 |
| 2,886,772 | 5/1959 | Gresham | 324/241 |
| 3,103,976 | 9/1963 | de Vries et al. | 324/207 |
| 3,197,693 | 9/1965 | Libby | 324/225 |
| 3,237,446 | 3/1966 | Wood | 324/226 |
| 3,328,681 | 6/1967 | Wood | 324/225 |
| 3,337,796 | 8/1967 | Hentschel et al. | 324/233 |
| 3,343,079 | 9/1967 | Crouch | 324/227 |
| 3,379,970 | 4/1968 | Kusenberger et al. | 324/220 |
| 3,401,332 | 9/1968 | McClurg et al. | 324/227 |
| 3,529,236 | 9/1970 | Proctor | 324/260 |
| 3,538,433 | 11/1970 | Wood et al. | 324/227 |
| 3,543,144 | 11/1970 | Walters et al. | 324/221 |
| 3,555,412 | 1/1971 | Fowler | 324/228 |
| 3,579,099 | 5/1971 | Kanbayashi | 324/235 |
| 3,609,530 | 9/1971 | Johnson | 324/225 |
| 3,612,987 | 10/1971 | Placke et al. | 324/242 |
| 3,693,075 | 9/1972 | Forster | 324/229 |
| 3,835,374 | 9/1974 | Frost | 324/220 |
| 3,843,923 | 10/1974 | de Vries | 324/228 |
| 3,916,301 | 10/1975 | Vild et al. | 324/226 |
| 3,940,689 | 2/1976 | Johnson, Jr. | 324/221 |
| 4,061,967 | 12/1977 | Hall | 324/260 |
| 4,079,310 | 3/1978 | Osborne et al. | 324/226 |
| 4,096,437 | 6/1978 | Kitzinger et al. | 324/227 |
| 4,101,832 | 7/1978 | Baker et al. | 324/227 |
| 4,247,819 | 1/1981 | Shimanda et al. | 324/233 |
| 4,270,088 | 5/1981 | Weischedel | 324/241 |
| 4,292,588 | 9/1981 | Smith | 324/221 |
| 4,292,589 | 9/1981 | Bonner | 324/221 |
| 4,379,261 | 4/1983 | Lakin | 324/232 |
| 4,485,344 | 11/1984 | de Sivry et al. | 324/207 |
| 4,492,115 | 1/1985 | Kahil et al. | 324/229 |
| 4,538,108 | 8/1985 | Huschelrath et al. | 324/232 |
| 4,555,665 | 11/1985 | Stanley et al. | 324/229 |

FOREIGN PATENT DOCUMENTS 913780 12/1962 United Kingdom.

Primary Examiner—Reinhard J. Eisenzopf
Assistant Examiner—Walter E. Snow
Attorney, Agent, or Firm—Norvell & Associates

[57] ABSTRACT

A method and apparatus for determining the extent of defects in ferromagnetic tubular elements comprising a continuous string for use in an oil or gas well is disclosed. The tubing trip tool measures tubing average wall thickness, local defects, such as corrosion pitting, and axial defects, such as sucker rod wear during removal of the tubing from the well. Tubing velocity is also measured, and couplings between tubing sections are detected and counted, in order to specify the axial location of defects on each tube, and also provide a profile of the condition of the overall string. A saturating magnetic field and a fluctuating magnetic field are applied to the tubing and the magnitude of the induced fields and the changes are measured to quantify defects in the tubing.

67 Claims, 26 Drawing Figures

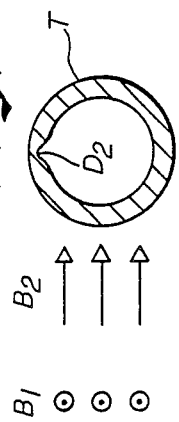
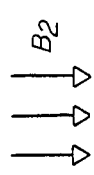
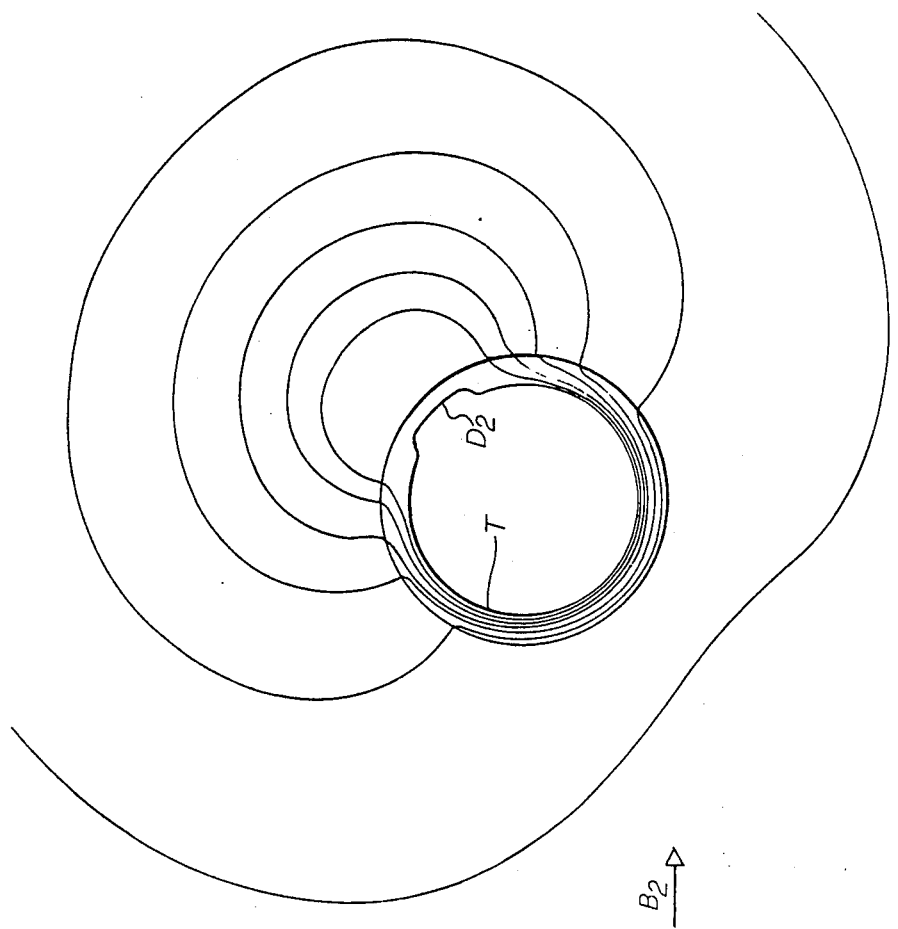

METHOD AND APPARATUS FOR MEASURING DEFECTS IN FERROMAGNETIC ELEMENTS

BACKGROUND OF THE INVENTION

1. Field of the Invention

This invention relates to defect inspection of tubular elements comprising a generally continuous tubular string used in a subterranean oil and gas well, and more particularly to inspection of tubular elements by detecting the properties of magnetic fields induced in the tubular elements during removal from the well.

2. Description of the Prior Art

Continuous tubular strings formed of connectable tubular sections or elements, such as production tubing strings, strings of drill pipe and casing strings, are used in the drilling, completion and production of subterranean oil and gas wells. The tubular elements comprising such strings are subject to mechanical damage while the tubular elements are located within the well and are also subject to the action of corrosive fluids which may be contained within the tubular elements or which may be transported through the tubular string between the well surface and a downhole location. It is therefore advantageous that the individual tubular elements comprising a tubular string be inspected periodically. Commonly, tubular elements or tubular sections are inspected for defects after the tubing string is removed from the well. Conventional inspection of tubular sections normally occurs after the individual tubing sections comprising the tubing string have been disengaged. Defect inspections are conventionally performed on a section by section basis. Occasionally, inspection is performed downhole through the use of inspection calipers. These tools leave "caliper tracks" and can be affected by the contents of the tubing.

A number of techniques exist for determining the presence of a defect in a tubing section. For example, the precise location of internal and external radially extending and three dimensional defects, including slug inclusions, mechanical damage, corrosion pitting and fatigue cracks, has been determined by flux leakage techniques in which a longitudinal magnetic field is induced by one or more magnetic induction coils. Surface riding detectors are located around the tubing and the maximum signal is recorded to precisely locate the defect. Since this magnetic inspection is conducted on a section by section basis after disengagement from the tubing string, when surface dirt, scale and mud can be controlled, detectors can be placed directly on the surface of the ferromagnetic tubular section to determine the presence of defects.

The location of longitudinal defects, including internal and external seams, plug scores, eccentricity, wear due to sucker rod interference, and wireline cuts, has been detected by inducing a circumferential magnetic field in the tubing. The field is induced by a high current discharge through an insulated rod on the interior of the tubing section. Detectors rotating around the surface of the tubing locate these longitudinal defects. Again, since the inspection is conducted on a section by section basis, the insulated rod can be inserted through the interior of the tubing section for this longitudinal defect inspection technique.

Other conventional inspection systems use methods which do not require insertion of rods and probes inside the pipe. Specifically, a common way of detecting longitudinal defects magnetically is the "rotating pole" method, where the magnetic field is applied from the outside by rotating electromagnets, and detectors positioned in-between the poles scan the outside surface of the pipe.

Tubing wall thickness has been measured by measuring the radiation from a rotating radioactive source of gamma radiation transmitted through the wall of a tubing section. For example, with a source rotating around the pipe, a detector may be located on the inside of the pipe to determine the degree of attenuation of gamma radiation and thus to determine the wall thickness. Again, this technique requires access to individual tubing sections after disengagement of the string. Other ways of measuring wall thickness with gamma radiation, which are backscatter, double-wall through-transmission and chord, have both the radiation detector and the source located on the outside of the pipe. Radiation methods introduce such problems as radiation licensing, record keeping, radiation safety administration, source handling complications, and fear of the unknown.

Techniques requiring surface-riding detectors, insertion of a detector or a driving means within the bore of tubular elements or requiring rotating mechanical means to obtain a complete circumferential coverage of tubing sections are unsuited for use in defect inspection and measurement of tubing sections while the string is being removed from the well. These defect inspection techniques are also unsuited to the measurement of defects in tubing sections while the sections are interconnected in the tubing string. Thus these inspection techniques are not suitable for use on a drilling, completion or workover rig at the surface of the well to measure defects in a tubing string as the string is removed from the well. In addition to the requirements that only disengaged tubing sections be individually measured, additional problems which would be encountered are the limited space available on the rig, the inability to control the longitudinal velocity of the tubing string as it is removed from the well, and the difficulty in precisely controlling the transverse location of the tubing sections comprising the tubing string. Furthermore, the use of surface detectors in a tubing trip tool for measuring defects as tubing sections, comprising a tubing string, are removed from the well is also complicated by the presence of solid deposits, such as drilling mud, and tubing mounted components, such as retrievable packers, which may be incorporated into the tubing string.

One technique for inspecting tubular elements which is adaptable to relative movement, at variable velocities, is a technique involving the use of a saturating longitudinal magnetic field and the subsequent measurement of the time integral of the electrical signal caused by the magnetic field applied to the ferromagnetic tubular member to determine the average wall thickness. Testing using this technique has been conducted for surface pipe installations in which the magnetic field and the flux detecting elements are moved relative to a continuous pipe array. Such apparatus has not, however, been employed to measure the average wall thickness of tubing sections as they are removed from an oil or gas well.

SUMMARY OF THE INVENTION

The method and apparatus disclosed herein is used to determine the extent of defects in ferromagnetic tubular elements comprising a continuous string used in an oil or gas well. The tubing trip tool measures tubing average wall thickness; local defects, such as corrosion pitting; and axial defects, such as wear due to sucker rod interference, during removal of the tubing from the well.

A uniform magnetic property is induced in at least a portion of the tubing. In the preferred embodiment, an appropriate longitudinal magnetic field is induced by applying an appropriate uniform magnetizing field. The magnitude of the electric signal integral from this field determines the tubing wall thickness.

Flux leakage in the longitudinal magnetic field is related to the presence of local defects, such as corrosion pitting. The shape of the flux leakage field is determined, for example by geometric signal processing, to quantify the depth of the local defects. In the preferred embodiment, multiple flux leakage detecting elements, such as Hall effect probes, are used to determine two different derivatives of the flux leakage, and the depth of the local defects, such as corrosion pits, is a function of both different derivatives evaluated at their local maximums.

The presence of axial defects, having an axial dimension in excess of the local defects is determined by applying a fluctuating magnetic field in addition to the first uniform magnetic field. Driven fields induced in the tubing element by the fluctuating field are then used to measure the axial defects. In the preferred embodiment the fluctuating fields are generated by two coils having sinusoidal conductor distributions of different phases around the tubing. The driven fields are also detected by using two sinusoidal detector coils having sinusoidal conductor distributions of different phases. The applied fluctuating field is rotated around the tubing using stationary coils and the presence of axially extending defects at various angular positions can be detected.

BRIEF DESCRIPTION OF THE DRAWINGS

FIGS. 14 and 15 are views similar to FIG. 13 showing the differential field lines for different orientations of an axially extending defect relative to the driving magnetic fields.

FIGS. 16-19 illustrate the rotation of the fluctuating magnetic field around a tubular element to detect axially extending defects at different angular positions relative to the driving magnetic field.

DESCRIPTION OF THE PREFERRED EMBODIMENTS

Tubing Trip Tool

Figure 1:
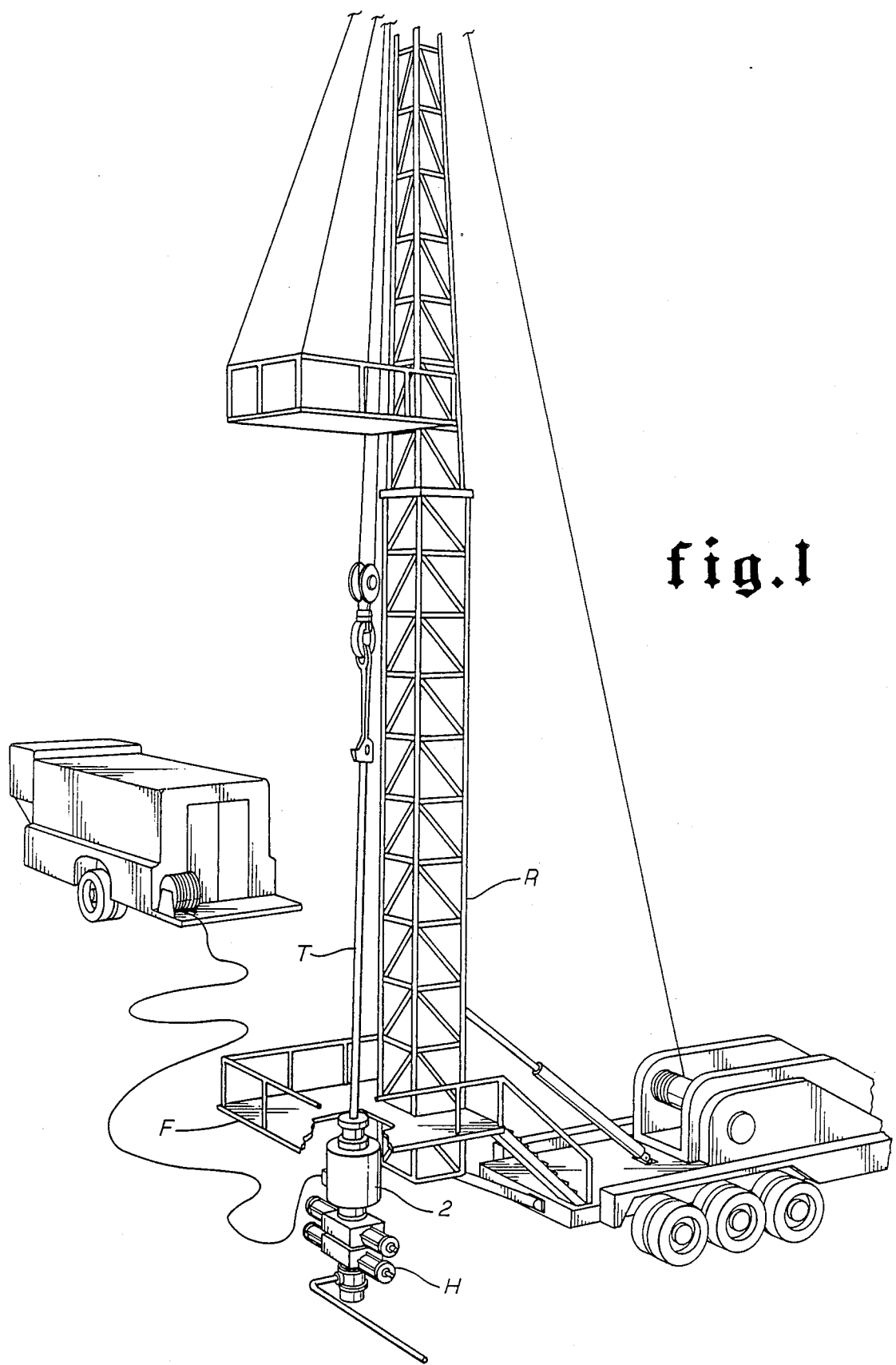
FIG. 1 is a schematic of the tubing trip tool on a surface rig.

A conventional workover rig illustrated schematically by rig R in FIG. 1, is used to remove a tubular string, such as a casing, drilling or tubing string represented by tubing string T, from an oil or gas well during workover operations. Workover operations normally involve the removal of the tubular string to permit operations intended to restore or increase production in a producing well. Typically the original tubing string is reused if the respective tubular elements are in satisfactory condition. FIG. 1 illustrates the use of a tubing trip tool 2 at the rig site to measure defects in each tubular element as it is removed from the well. A tubing trip tool 2 comprising the preferred embodiment of this invention can be positioned on the wellhead H below the rig floor F so as not to interfere with conventional operations on the rig. The tubing trip tool can be attached directly to the blow out preventers on the well.

Figure 2:
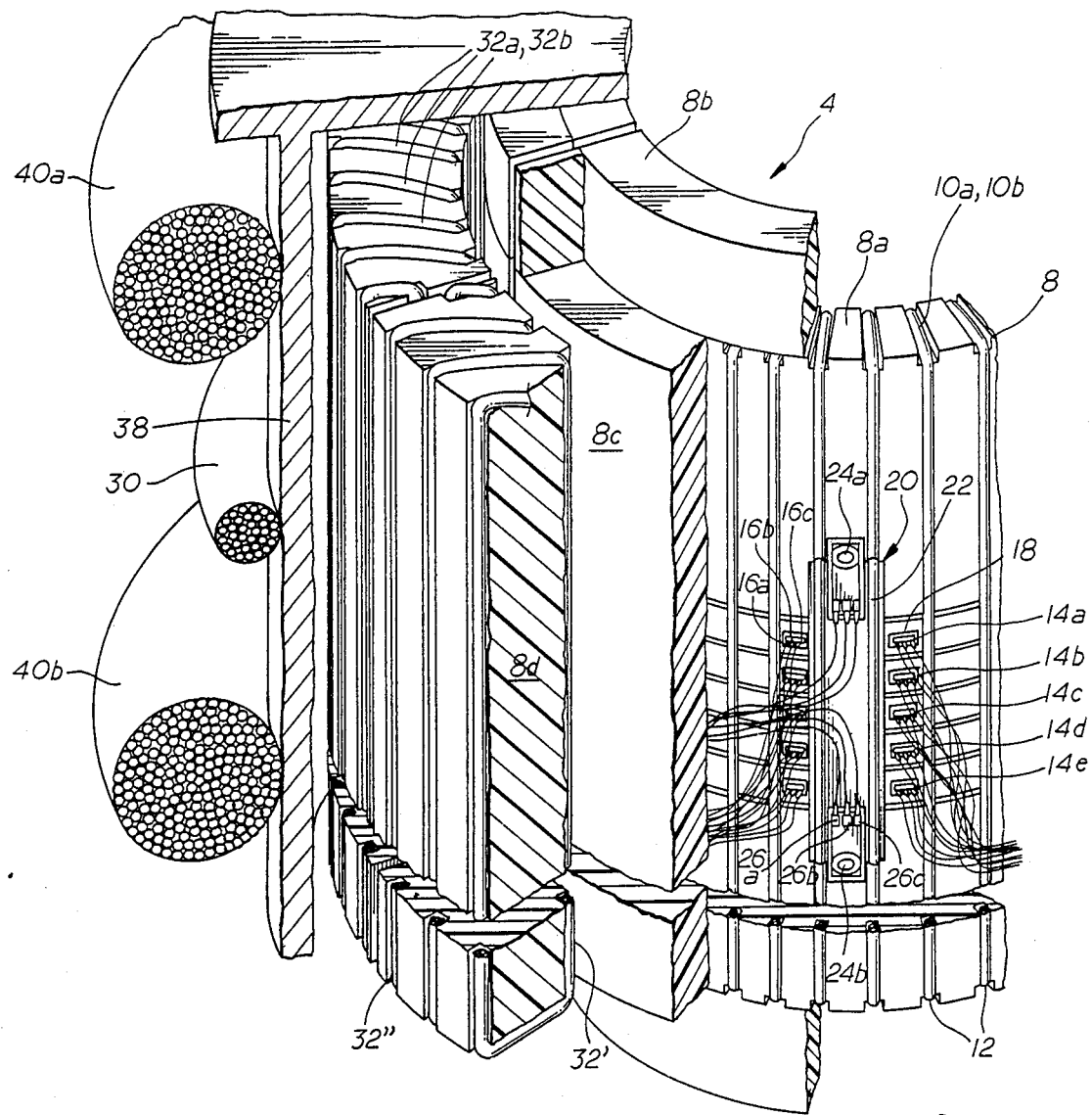
FIG. 2 is a view of a segment of the tubing trip tool in the expanded configuration.
Figure 3:
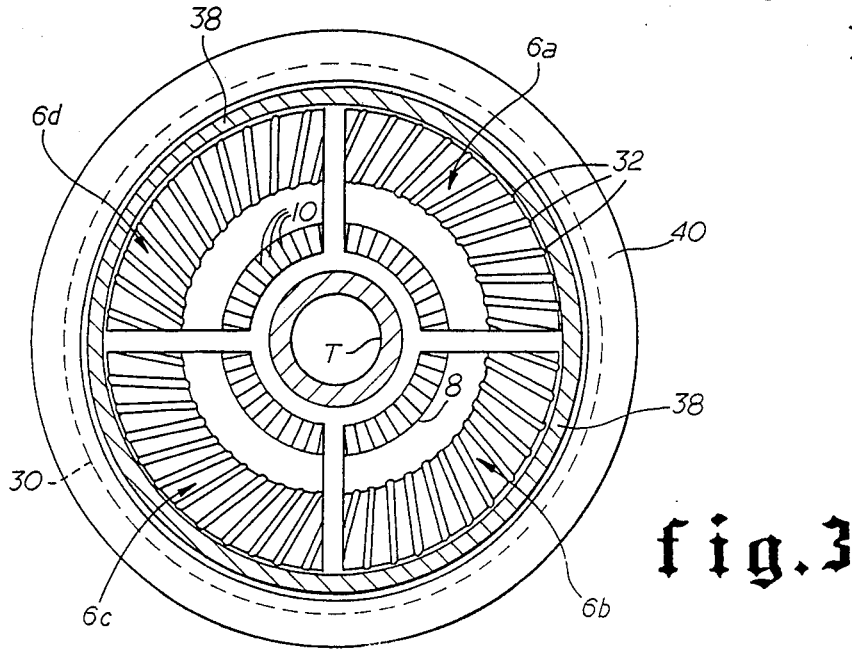
FIG. 3 is a cross-sectional view of the tubing trip tool head in the expanded configuration.

A segment of the tubing trip tool head 4 is shown in FIG. 2. The head includes two separate driving coils, two separate detecting coils, and a plurality of discrete detecting elements to determine the extent of defects in the tubing sections. A velocity detector for determining relative velocity between the head and tubing sections is also included. The preferred embodiment of this invention comprises an expandable head having four segments 6a-6d as seen in FIG. 3. Each segment is an encasement 8 which comprises multiple components. The encasement 8 is fabricated from a material that has the properties of an electrical insulator. In the preferred embodiment of this invention, encasement 8 can be formed from an encapsulation material or potting compound which will insure that the proper amount of space is maintained between the electrical components. The encapsulation material will occupy any spaces or voids surrounding the components, and will provide a barrier between the electrical components and the atmosphere surrounding encasement 8, thereby rendering encasement 8 safe for use on the wellhead where explosive vapors can be encountered.

Two separate AC detecting coils 10a and 10b are carried on the innermost insulating body section 8a. The circumferentially continuous coils 10a and 10b are wound in appropriate grooves on body section 8a and a plurality of separate loops are formed around body 8a. These separate loops, each of which contains conductors forming the separate detecting coils 10a and 10b, are positioned in a radial plane on encapsulating member 8a. Each loop is generally defined by two radially spaced, axially extending coil conductor sections and two axially spaced, radially extending coil conductor sections. The coil conductors then define an annular volume encircling the tubular sections passing axially therethrough. Radially extending planes between the coil conductors will be generally perpendicular to magnetic field lines detected by coils 10a and 10b as will be subsequently more completely discussed.

A plurality of flux leakage detecting elements 14a–14e are also located in the inner encapsulating body section 8a. In the preferred embodiment of this invention, each of the flux leakage detecting probes 14a–14e comprises a separate probe in which voltage is generated in response to the Hall effect. The plane of each Hall probe is perpendicular to the axis of the tubing trip tool head 4 and is located perpendicular to each tubular element moving axially relative to the tubing trip tool head 4. In the preferred embodiment of this invention, separate groupings of five Hall effect flux leakage detecting probes are positioned at different angular positions around the tubing trip tool head 4. Each of the Hall probes 14a–14e is received within corresponding slots 18 extending into the insulating body section 8a. In the preferred embodiment of this invention, five equally spaced probes are positioned at each angular location.

One or more velocity detectors 20 is positioned on the exterior of insulating body section 8a. In the preferred embodiment of this invention, each velocity detector 20 comprises a detector circuit or coil 22 having two or more Hall probes 24a and 24b located within the circuit. The plane of the velocity detector circuit or coil 22 is perpendicular to a radial plane extending through the tubing trip tool head 8. The plane of the individual Hall probes 24a and 24b in the velocity detector is perpendicular to the plane of the Hall probe 14a–14e used for flux leakage detection.

The AC magnetic detecting coils 10a and 10b, the flux leakage detecting probes 14a–14e and the velocity detector 20 are each radially spaced from the tubing element T in which defects are to be measured. In the segmented embodiment of the invention shown in FIG. 2, the individual segments can be shifted radially from a measuring position to an outer position to permit obstructions to move past the tubing trip tool head. Each of the detector coils is, however, spaced from the surface of the tubing T in the inner measuring position. In the preferred embodiment of this invention, the inner surface of the tubing trip tool head 4 is positioned approximately two-thirds of an inch from the surface of the tubing element T. Insulated body sections 8b and 8c surround the detecting coils and probes mounted on insulating body section 8a. Epoxy or some other potting material can also be used to insure that all potentional electrical leakage paths are appropriately isolated from each other and from the atmosphere.

Outer AC driving coils 32a and 32b are positioned around insulating body section 8d. The AC drive coils 32a and 32b each comprise continuous coils having an angular conductor distribution similar to that of AC detecting coils 10a and 10b. The sinusoidal distribution in the coils 32a and 32b is relatively offset so that the conductor distribution phase differs between drive coils 32a and 32b. In the preferred embodiment of this invention, the conductor distribution is offset by 90° so that coil 32a can be referred to as a sine coil and coil 32b can be referred to as a cosine coil. Coils 32a and 32b each completely encircle the tubing trip tool head 4 and tubular element T with separate loops, containing conductors from each coil 32a and 32b, being formed in radial planes around the tubing trip tool head 4. On the exterior, AC driving coils 32 are encapsulated within the common encapsulating insulating body 8 of the tubing trip tool 2.

In the preferred embodiment of this invention, an outer metal sheath 38 can be positioned around the exterior tubing trip tool head. This outer metal sheath, which can be fabricated from a nonferromagnetic material, such as aluminum, serves as a carrier for the outer DC drive coils 40a and 40b and for encircling coil 30. In the preferred embodiment of this invention, the DC drive coils are separated into two separate bundles. A single drive coil bundle can also be used. The encircling drive coils 40 contain a sufficient number of amp turns to saturate the tubular element T passing through the tubing trip tool. Encircling coil 30 extends completely around the circumference of the tubing trip tool head 4 and surrounds the tubular element T at a greater radial spacing than the detecting elements 10a and 10b, 14a–14e, and 20.

Figure 4:
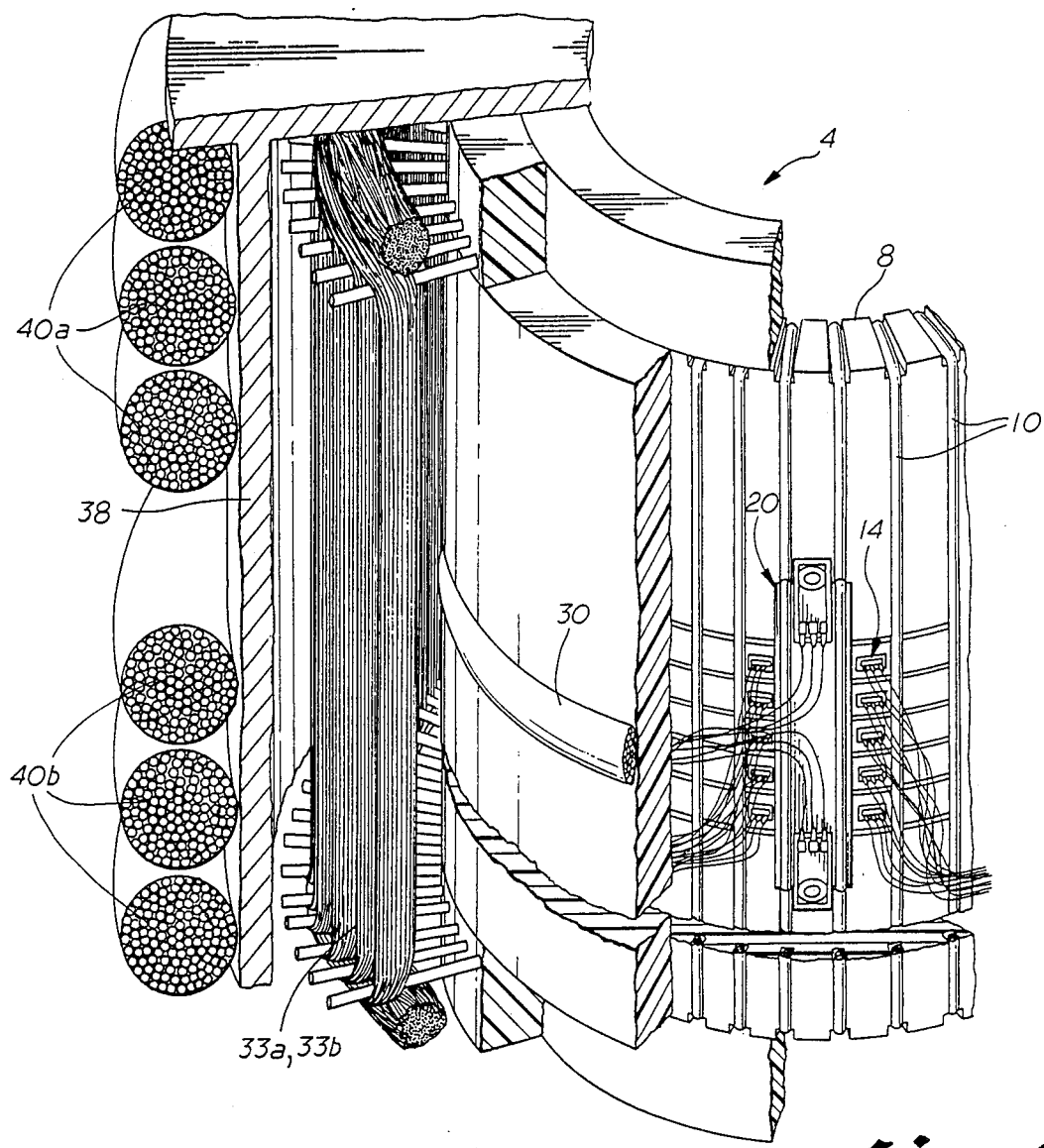
FIG. 4 is a view of an alternate embodiment of the tubing trip tool shown in FIG. 2.
Figure 5:
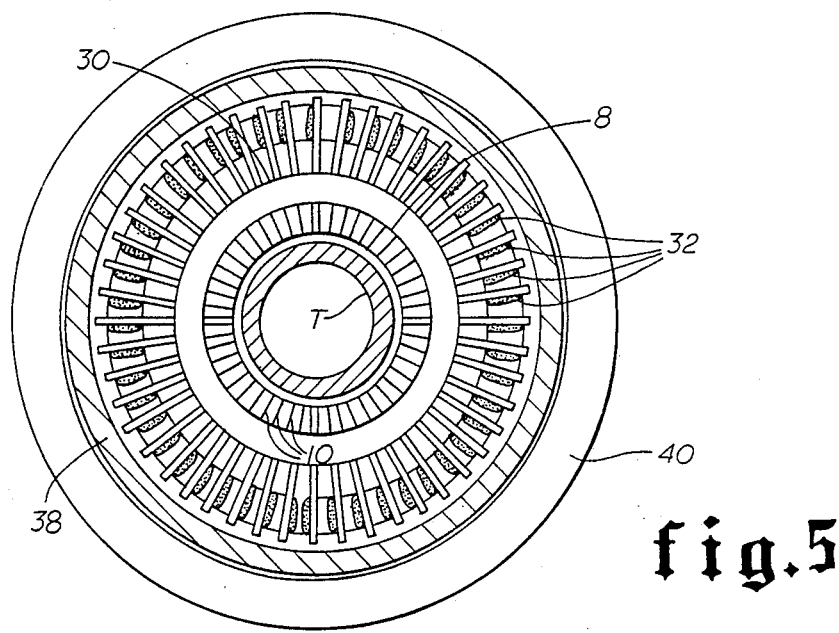
FIG. 5 is a cross-sectional view of the tubing trip tool head shown in FIG. 4.
Figure 6:
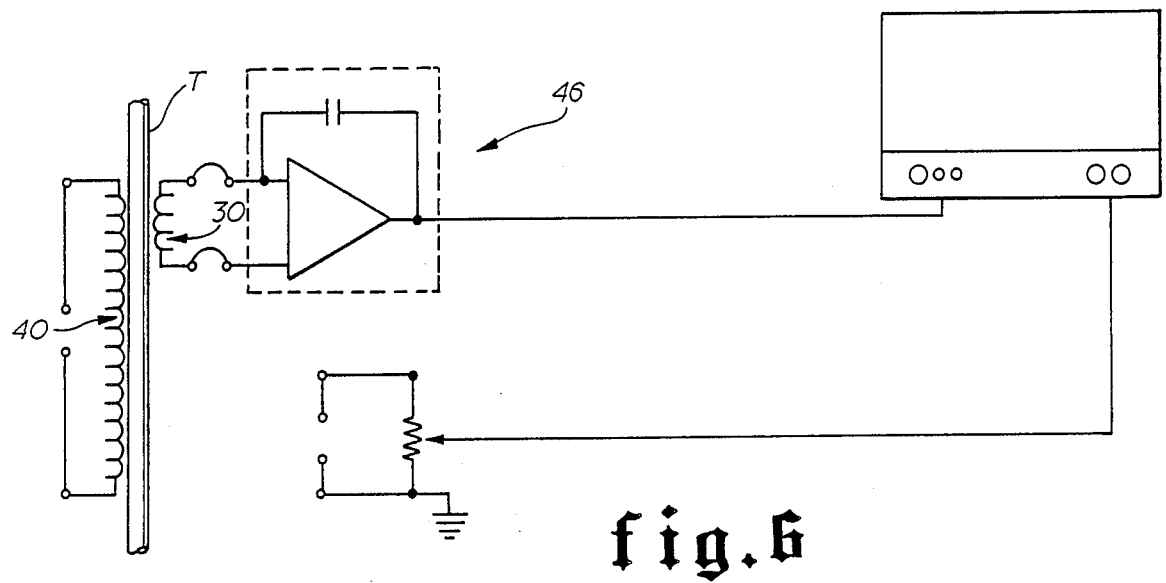
FIG. 6 is a view showing the wall thickness measurement circuitry.

The alternate embodiment of FIG. 4 and FIG. 5 is similar, in most respects, to the tubing trip tool head shown in FIGS. 2 and 3. The tool of FIG. 4 comprises a single unitary head which is not expandable. The tool of FIG. 4 has AC driving coils 33 fabricated in a different manner than the driving coils in FIG. 2. The two coils 33a and 33b do have a sinusoidal conductor distribution around the exterior of the tubular element 2. Coils 33a and 33b are not, however, wound in the same radial loop fashion as are coils 32a and 32b. Coils 33a 33b are fabricated by initially extending a conductor in a first axial direction after which the conductor is wrapped around a semi-circular portion of the tubing trip tool. The conductor then extends in the opposite axial direction along the opposite surface of the tool head. The axial portion of the separate conductors are, however, distributed around the angular distribution in a sinusoidal fashion. The sinusoidal distribution of conductors 33a and 33b can be obtained by using only half the amount of conductor as would be necessary to fabricate drive coils 32a and 32b in FIG. 2. The orientation of the conductors 33a and 33b does, however, interfere with the expansion and segmentation of the tubing trip tool head.

Wall Thickness Measurement

The tubing trip tool 2 measures the wall thickness of a tubing section by using a technique in which the total flux induced in the tubing section by a saturating magnetic field is measured. The ferromagnetic tubing section within the saturating magnetic field is saturated when the magnitude of the magnetic field induced in the ferromagnetic element is at a maximum and does not increase as a result of a further increase in the saturating magnetizing field. Thus the saturating magnetizing field can produce a uniform saturated magnetic field in a tubing section having a specified cross-sectional area. In other words, the total magnetic flux is dependent upon the cross-sectional area or wall thickness of the tubular section. If the saturating magnetizing field is uniform, the contribution of the total flux induced by the magnetization of the pipe material within a given area varies as the cross-sectional area of the tubing section. By providing a large number of amp turns in a coil 40 encircling a tubing section, a saturated magnetic field extending longitudinally within the wall of the tubing section can be produced.

The total flux through an area intersecting the axis of the tubing section and intersecting the longitudinal saturated magnetic field can be measured by pickup coil 30 encircling the tubular section. The area of the pickup coil would preferably, but not necessarily, be perpendicular to the axis of the tubing section. The total flux through the pickup coil can be detected by signal integration. The EMF induced in a pickup coil is directly related to the time rate of change of the flux through the coil. Thus the total flux can be detected by integrating the EMF produced in the coil over time. In fact, a virtually linear dependence of the total flux through the pickup coil with average wall thickness can be obtained. Thus a convenient direct measurement of average wall thickness can be made.

In the tubing trip tool 2, the saturating magnetizing field is applied by one or more DC drive coils 40. In the preferred embodiment of this invention, two drive coils 40a and 40b are positioned on the exterior of the tubing trip tool head 4 (see FIGS. 2 and 26). The pickup coil 30 encircling the tubular section T detects the total flux, and the output of pickup coil 30 can be attached to a conventional integrator 46. The output voltage of the integrator is a direct measure of tubing wall thickness. If the tubing moves axially relative to the stationary staturating magnetizing field, a continuous measurement of total flux will result in a measurement of the wall thickness along the length of the tubing section. Conventional signal processing means can be used for comparing and correlating detected signals with average wall thickness.

This noncontact measurement of average wall thickness can be incorporated into the tubing trip tool 2 comprising the preferred embodiment of this invention. A sufficiently strong and uniform DC magnetizing field can be produced by a sufficient number of amp turns in coils 40a and 40b. For example, approximately 5,000 amp turns can saturate a 2⅜" OD pipe, a standard size tubing section used in an oil and gas well. In the preferred embodiment of this invention, a sufficient uniform longitudinal saturated magnetic field is produced in a tubing section moving relative to the saturating magnetic field within a range of velocities normally encountered in the removal of a tubing string from an oil or gas well. A coil having an overall height of less than one foot has been found to satisfactorily produce a longitudinal saturated DC magnetic field in the tubing section and an accurate measurement can be obtained of the average wall thickness.

Local Defect Detection

The average wall thickness of a ferromagnetic tubular member or pipe can be determined by detecting the total flux induced by the saturating magnetizing field within the element. Qualitative information as to the changes in surface texture due to such factors as internal and external corrosion, can be determined by comparing average wall thickness at different locations on the tubular member. The difference between the signals produced in separate coils will not yield quantitative information as to the state of local defects in the tubular members.

In tubular sections used in oil and gas wells, corrosion on the tubular member can result in localized corrosion pits $D_1$ which can seriously reduce the strength of individual tubing sections. Since the thickness of the remaining wall of the tubular sections determines the ability of individual tubular sections to function in the work environment, the depth of local corrosion pits must be quantified to determine the acceptability of the tubular sections.

It is common practice to grade used tubing based upon the depth of corrosion pits. Although each separate corrosion pit would constitute a local defect D1, the dimensions of which would generally be less than the diameter of the tubular element, the nature of the corrosion phenomenon would result in a plurality of irregular and overlapping corrosion pits being located in the same general region on the interior of a tubular section. Of course the flux leakage will be dependent upon the overall size of individual corrosion pits and not just the depth of the corrosion pits. Thus the length and width of the corrosion pits would affect the flux leakage detected. Other factors, such as the contour or shape of the corrosion pits and the extent of any discontinuities in the shape of corrosion pits, would also affect the flux leakage. Thus the leakage fields of different pits having the same depth in a tubular section will differ for different lengths and widths of the pits as well as for a different contour of the pits. Background fields or noise due to unrelated phenomenon can also affect the signal corresponding to flux leakage and the saturated magnetic field within the pipe.

In the preferred embodiment of this invention, a plurality of flux leakage detecting elements 14 are disposed within the saturating magnetizing field. These flux leakage detecting elements are disposed at a plurality of axially spaced positions within the saturating magnetizing field. In the preferred embodiment of this invention, a plurality of discrete probes having an output produced by the Hall effect are used. In the preferred embodiment of this invention, identical flux leakage detecting Hall probes 14a–14e are equally spaced at five separate axial positions. Although only two sets of flux leakage detecting Hall probes 14a–14e are shown in FIG. 2, it should be understood that corresponding sets of multiple elements are circumferentially disposed around the tubing trip tool head to provide complete coverage around the periphery of the tubular element to detect local defects, such as corrosion pits located at different angular positions.

In the preferred embodiment of this invention, the individual flux leakage detecting Hall probes are oriented such that the plane of the Hall sensing element is perpendicular to the axis of the moving tubular element. Hall elements, such as the type used herein, produce an output voltage proportional to the product of the input current, the magnetic flux density, and the sine of the angle between the magnetic flux density and the plane of the Hall generator. Thus a maximum voltage output from a given leakage field would be produced by orienting the individual flux leakage detecting Hall probes perpendicular to the saturated magnetic field. The DC drive coils 40a and 40b are positioned to induce a longitudinal or axial saturated magnetic field within the tubular element T. By orienting the probes 14a–14e perpendicular to the longitudinal saturated magnetic field within the pipe, the flux leakage detecting probes are situated to detect longitudinal changes in the magnetic field. Of course transverse magnetic field changes would also occur as a result in the change in the longitudinal saturated field within the tubular member. Orientation of flux leakage detecting Hall probes perpendicular to the radius of a moving tubular section would be ideal to detect these transverse field changes. However, it is understood by those skilled in the art that the transverse magnetic field changes are related to longitudinal magnetic field changes. Thus a plurality of individual flux leakage detecting Hall probes oriented at right angles to the probes 14a-14e used in the preferred embodiment of this invention could also be used. Of course flux leakage detecting elements other than Hall probes can also be employed in the measurement of localized defects, such as the depth of corrosion pits. For example, the change in flux linking a coil will also result in a signal which can be employed for local defect measurement. However, the output signal from a coil must be integrated to obtain the same output independent of the velocity of the tubing element T, as would be obtained with a Hall probe.

It has been found that the magnitude of the flux leakage detected by elements 14 does not provide an adequate quantitative measure of the depth of local defects, such as corrosion pitting defects, on a tubular element. The fact that flux leakage is dependent upon the size and shape of localized defects, such as corrosion pitting, rather than upon the depth alone, is believed to account for the inability to measure localized defect depth by measuring flux leakage magnitude alone. However, it has been found if effects due to the length and width of defects, such as corrosion pitting, can be removed, the resulting signal results in an accurate measurement of the depth of the local defect.

In the preferred embodiment of this invention, a signal corresponding to the depth of local defects, such as defects due to corrosion pitting, can be determined by differentiation of the magnitude of the flux leakage relative to the axial or longitudinal dimension of the moving tubular member. A signal corresponding to the depth of local defects, such as defects due to corrosion pitting, can be obtained by comparing two derivatives of different orders, each with respect to the axial dimension of the flux leakage, obtained when the saturated magnetic fields at the maximum value of the flux leakage corresponding to each measured discontinuity. In the preferred embodiment of this invention, the second and fourth derivatives, determined by using finite element approximations, can be combined to produce a signal measuring the depth of the local defect. It has been found that the depth of a local defect can be measured in the following fashion.

$$d = k[(f'')^a / (f'''')^b]$$

; where
d is equal to the depth of local defects, such as a defect due to corrosion pitting.
k is an empirically determined proportionality constant.
$f''$ is the second derivative of the flux leakage with respect to the axial or longitudinal dimension.
$f''''$ is the fourth derivative of the flux leakage with respect to the axial dimension.
a is an empirically determined factor.
b is an empirically determined factor.

Of course other similar empirically determined relationships between the two non-zero derivatives might be used by those skilled in the art to obtain local defect depth without departing from the spirit of this invention. For the relationship employed herein, care must be taken that non-zero derivatives be used to avoid dividing by zero. The derivatives employed herein are being evaluated at their *maximum* where they are inherently non-zero.

Figures 7, 8:
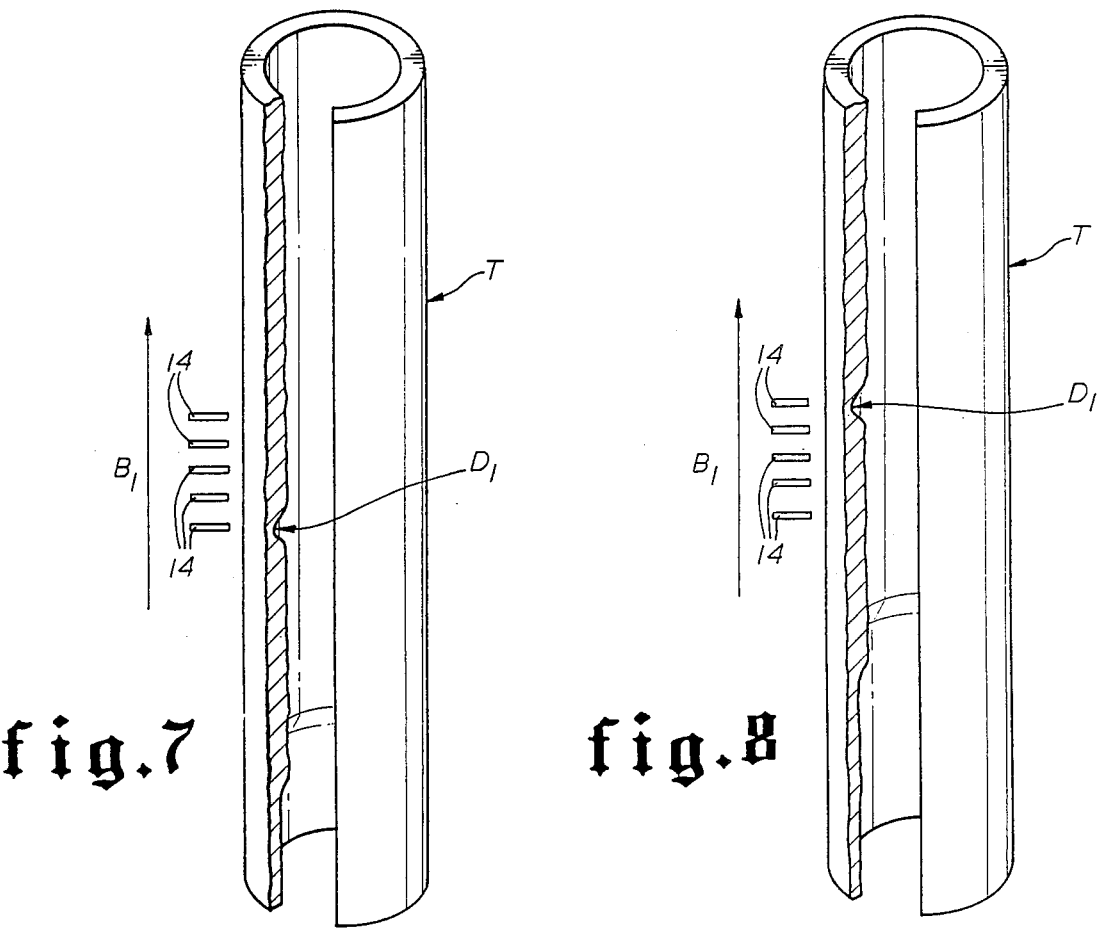
FIG. 7 is a schematic of the tubing string and the detectors for measuring local defects.
FIG. 8 is a view similar to FIG. 7 showing relative movement of the tubing.
Figure 9:
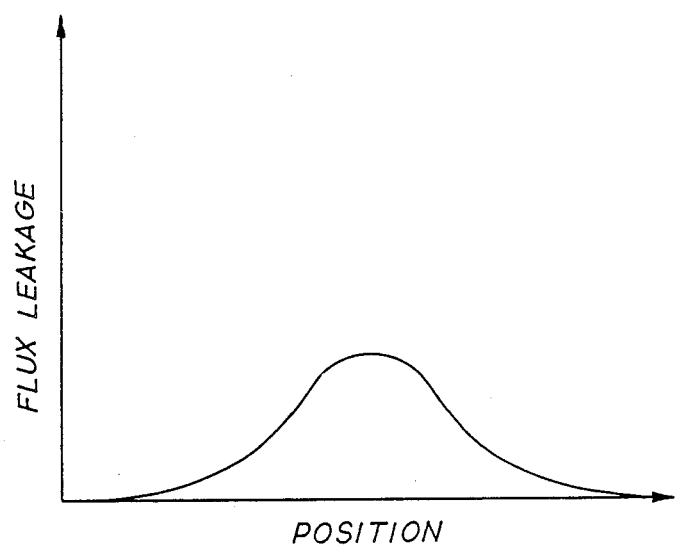
FIG. 9 shows the effect of movement of the tubular element upon flux leakage.

In the preferred embodiment of this invention, the geometric filtering or numerical differentiation is obtained by using a plurality of axially evenly spaced flux leakage detecting elements 14a-14e which remain fixed relative to each other (See FIGS. 7 and 8). By multiplying the magnitude of the flux leakage simultaneously detected in each element by appropriate factors and summing, the value of each of the higher order derivatives can be determined. In the preferred embodiment of this invention, the factors used to multiply the output of individual flux leakage detecting elements are constants and are chosen such that the value of each of the derivatives will be zero if the flux leakage is unchanging. The conventional voltage generating flux leakage detection elements 14a-14e employed in the preferred embodiment of this invention are spaced apart and a simultaneous value of flux leakage is obtained from each flux leakage detecting element 14. By detecting the value of flux leakage on opposite sides of the center, the value of the derivative in question may be obtained at the center location. Thus when the flux leakage reaches a maximum at the center of the detector array, the derivative of the appropriate order at the maximum flux leakage will be determined. This detector array will also evaluate the shape of the leakage field in the vicinity of the maximum flux leakage (See FIG. 9). By comparing non-zero derivatives of the flux leakage of different orders, the unchanging DC fields and that background noise which is basically unchanging with respect to the fluctuation of the flux leakage in the vicinity of a local defect will be reduced. Comparison of the non-zero derivatives will thus yield information as to the change in the saturated magnetic field due to flux leakage and will also give information on the shape and extent of the corrosion pitting field, from which information as to the length and width of the local defect, such as the length and width of a corrosion pit, will be eliminated. Thus the signal obtained from the differentiation and the comparison of different order derivatives will yield the signal which is proportional to the depth of a local defect.

It should be understood that similar information could be obtained by employing a single flux leakage detecting element and determining the magnitude of the flux leakage at each of the positions corresponding to the multiple elements 14a-e used in the preferred embodiment of this invention. However, the use of a single element to measure the flux leakage at separate positions would require an accurate determination of the exact position at which the multiple measurements were taken. For a detecting apparatus used to measure local defects in a tubular element which is not moving at constant speed, such a position indication would require an accurate measure of the velocity and hence position of the tubing element relative to the saturating magnetizing field. By using a plurality of elements rather than an individual detecting element, no velocity measurement is necessary for the measurement of critical parameters of local defects, such as the depth of a localized corrosion pitting defect.

The signals generated by the flux leakage field can be processed in a conventional manner to calculate the depth according to the generalized numerical derivative function presented herein or according to other algorithms measuring an appropriate variation of depth of a localized defect to the flux leakage obtained by numerical differential or by other geometric filtering means. Such signal processing can be performed by conventional analog or digital means for comparing and correlating signals to local defect depth, and appropriate signal processing circuitry can be incorporated to compensate for variations in the separate flux leakage detecting elements due to such factors as varying temperature sensitivities.

AXIAL DEFECT MEASUREMENT

The bore of a tubular member on tubing section T used in a tubular string in a subterranean oil and gas well can often have axially extending defects $D_2$ located at one or more circumferential positions on the tubing. An example of axially extending defects are defects due to sucker rod wear. Sucker rod wear on the bore of the tubing occurs when the sucker rod contacts the tubing during reciprocal movement of the sucker rod. However, sucker rod interference is not uniform around the circumference of the bore of the tubing section or tubular element. Sucker rod wear often occurs at only one circumferential location, although it is not uncommon for a sucker rod to oscillate laterally causing sucker rod interference at two opposite points. The loads placed on the individual sucker rod assembly will normally result in continual interference between the sucker rod and the tubing at the same locations.

Since the length of the sucker rod stroke is normally large compared to the diameter of the tubing, the length of the sucker rod defects can be expected to be greater than the diameter of the tubing. Although sucker rod wear is a common occurrence, points at which the sucker rod interferes with the bore of a tubing string may occur in only a fraction of the tubing sections if the distance between interferring sucker rod nodes is greater than the length of individual tubing sections. Not only must the tubing sections subjected to sucker rod wear be identified, but the depth of axial defects, such as sucker rod wear defects, must also be measured. The depth of the defects due to sucker rod wear is significant because the reduction in the strength of the individual tubing section increases with the depth of the axially extending sucker rod wear defect.

Axial defects $D_2$, such as defects due to sucker rod interference, can be detected by employing a fluctuating AC magnetizing field $B_2$ in addition to a uniform DC magnetizing field $B_1$. Even if a uniform DC magnetizing field in the longitudinal or axial direction is of sufficient intensity to saturate the ferromagnetic element or tubular section within the DC field, as is the case with the field used to determine wall thickness, the addition of a fluctuating AC transverse magnetic field will result in detectable changes in the magnetic state of the ferromagnetic element located within both fields. In fact, the DC field enhances the penetration of the AC field in the tubular sections. Of course the detectable changes resulting from the addition of the fluctuating transverse field will be dependent upon the geometry of the tubular element. For example, the response of an undamaged tubing section would differ from the response of a similar tubing section containing an axially extending defect, such as a rod wear interference defect. In the preferred embodiment of this invention, the changes due to such axially extending defects as sucker rod interference defects $D_2$ in an oil field tubular section can be detected even where the strength of the fluctuating transverse magnetic field is significantly less than the strength of a uniform saturating DC magnetizing field. It has been found that measurement of axial defects, such as sucker rod interference defects, can be made by applying a sinusoidal transverse magnetizing field having a frequency of approximately 100 Hz. and an intensity of appropximately 1/10th the intensity of a uniform saturating magnetizing field applied in the longitudinal direction. In the preferred embodiment of this invention, drive coils 32 are used to apply such a fluctuating magnetizing field.

Figure 12:
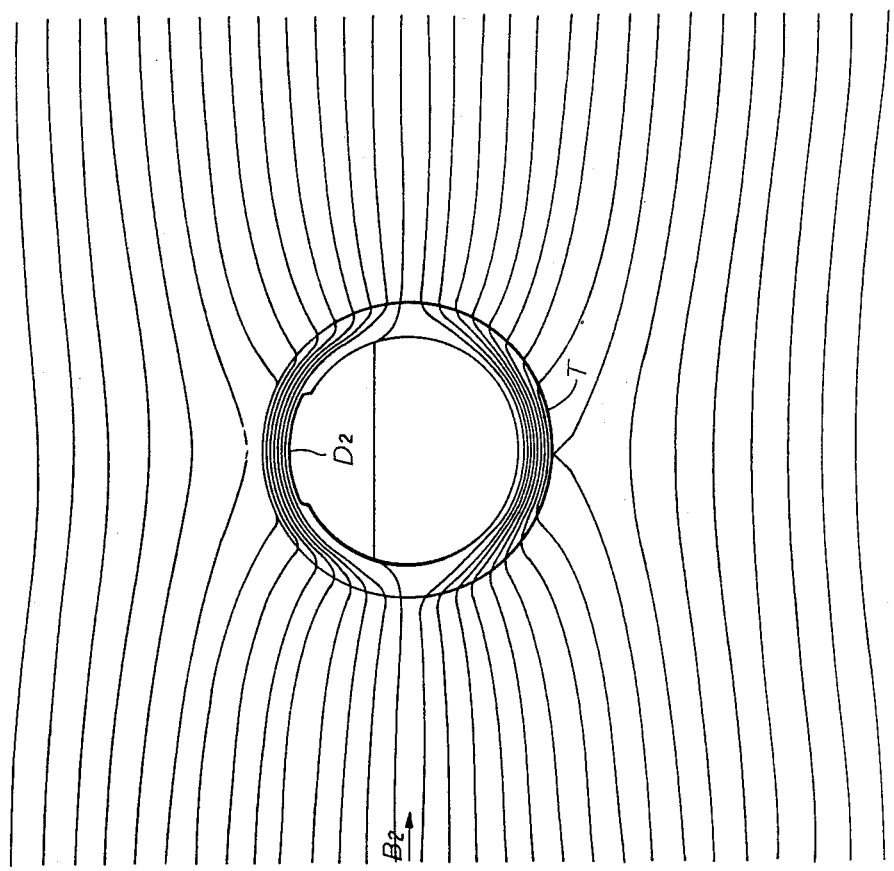
FIG. 12 is a view similar to FIG. 11 showing the total fluctuating magnetic field lines as effected by an annular section of a tubular element containing an axially extending defect on the internal surface of the tubular element.
Figure 11:
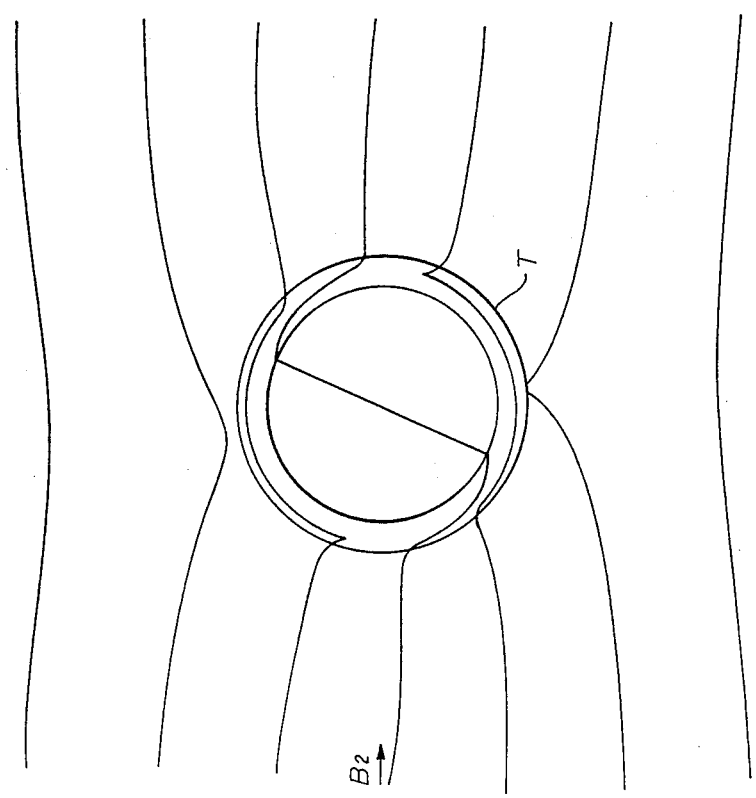
FIG. 11 shows the total fluctuating magnetic field lines as disturbed by the annular cross-section of a tubular element having no axially extending defects.
Figure 13:
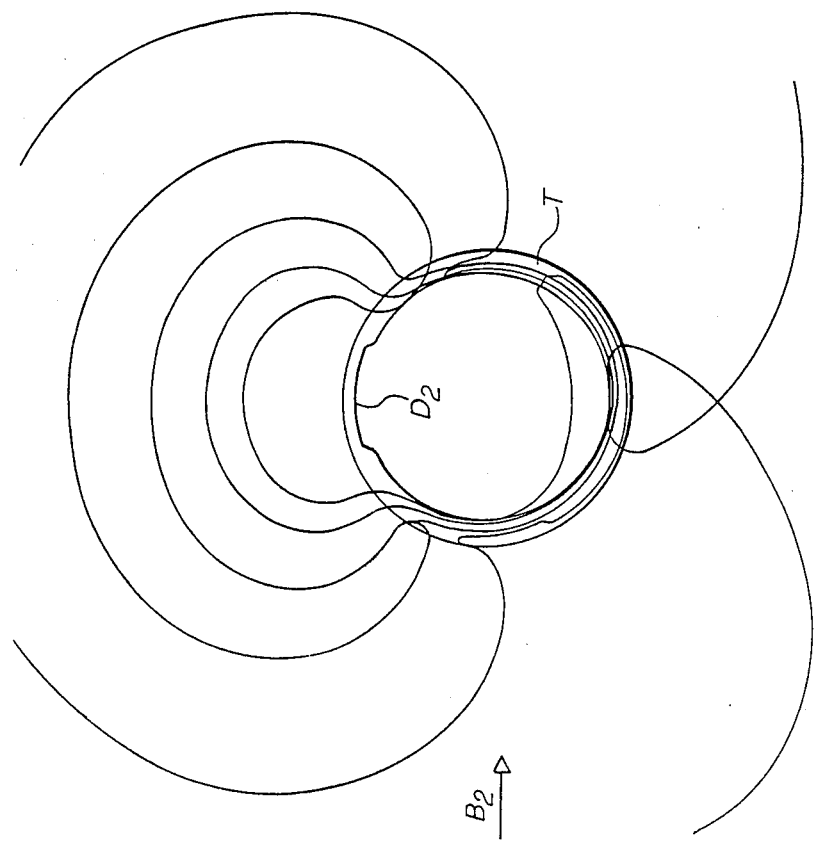
FIG. 13 is a view showing the difference in field lines between the magnetic fields shown in FIGS. 11 and 12.

Although the response due to the application of a transverse fluctuating magnetic field in addition to the uniform longitudinal saturating magnetic field will in part be due to flux leakage effects, the principle response will be due to eddy current effects. Eddy current effects will occur in both ferromagnetic and nonferromagnetic tubular members. The field changes resulting from the imposition of the fluctuating AC field are depicted in FIGS. 11-13. In FIG. 11, the magnetic field lines in a plane perpendicular to the axis of a tubular section are shown as they are effected by an undamaged annular section of tubing T. FIG. 12 shows similar magnetic field lines as effected by an annular section of tubing T which contains an axially extending defect $D_2$ located at one circumferential position on the bore of the tubing T. FIG. 13 shows magnetic field lines constituting the difference between the magnetic field around the undamaged annular section of FIG. 11 and the magnetic field lines around the damaged annular section of FIG. 12. The degree to which field lines of the type shown in FIG. 13 are generated is dependent upon the size of the axial defect $D_2$.

Figure 14:
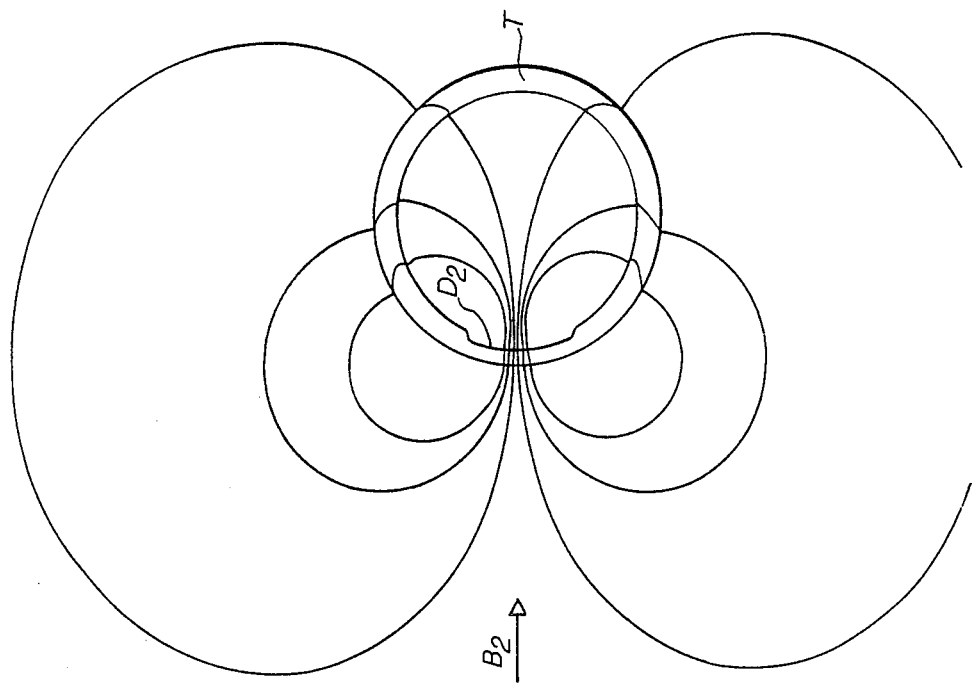

As shown in FIG. 13, the more significant, and therefore more easily measurable, changes in the magnetic field occur in the angular vicinity of the defect $D_2$. Of course the annular or circumferential orientation of defect $D_2$ relative to a fixed position in a detecting apparatus would be unknown. FIGS. 14 and 15 represent similar differential field lines which might occur when the defect $D_2$ is oriented at a different position relative to the fluctuating magnetic field $B_2$. Although it is not apparent from FIGS. 13-15, the degree of the magnetic response will depend upon the position of defect $D_2$ relative to the direction of the magnetic field. The differential magnetic field generated when the defect $D_2$ is oriented in the manner shown in FIG. 13 will be stronger than the differential field corresponding to the orientation of the defect in FIGS. 14 or 15.

In order to obtain full circumferential coverage of a tubular section and to obtain a measurable response, the preferred embodiment of this invention comprises an apparatus and method for rotating the fluctuating AC magnetizing field around the tubular section T as the tubing section moves axially relative to both the AC magnetizing field $B_2$ and the uniform DC saturating magnetizing field $B_1$. Thus the rod wear defect response measured in the preferred embodiment of this invention is due to an AC magnetizing field rotating around the tubing section and having a constant magnitude.

The rod wear detecting apparatus employed in tubing trip tool head 4 in the preferred embodiment of this invention can detect and measure rod wear defects $D_2$ at arbitrary circumferential positions in a tubing section or tubular element which may be moving axially at different and nonuniform velocities. When used in a tool for detecting rod wear defects as a tubing string is removed from an oil and gas well, the velocity of the tubing sections can be up to 300 feet per minute. Rotation of the magnetic field around the moving tubular sections to obtain complete circumferential coverage of the tubing sections cannot be practically accomplished by mechanically rotating the apparatus inducing the transverse fluctuating magnetizing field. In the preferred embodiment of this invention, rotation of the magnetic field is accomplished by employing separate phase windings in the drive coils 32 which generate the fluctuating transverse field. Thus the field is rotated electrically rather than mechanically. In the preferred embodiment of this invention, the drive coils 32a and 32b each have a conductor distribution which varies sinusoidally with the angular orientation around the drive coils. The conductor distributions in the two sinusoidal coils 32a and 32b are angularly displaced such that the phase of the conductor distribution in coil 32a differs from that in coil 32b. The sinusoidal drive coil as used in the preferred embodiment of this invention has a phase displacement equal to 90° so that coil 32a may be referred to as a sine coil and coil 32b may be referred to as a cosine coil. The space or angular displacement of the conductor distribution between the two phase windings and the time displacement of the current are such that a rotating field of constant angular speed and constant amplitude is generated. FIGS. 16-19 illustrate the rotation of the constant AC magnetic field $B_2$ in the presence of the constant DC magnetic field $B_1$ as the AC magnetic field rotates around the tubing section T containing an axial defect $D_2$.

It is apparent in FIGS. 13-15 that the disturbed or differential magnetic field lines due to axial defects $D_2$ as they appear in planes perpendicular to the moving tubing element T, are primarily circular. In the preferred embodiment of this invention, these differential field lines are detected by AC detecting coils 10a and 10b which are distributed around the circumference of the tubing trip tool head 4. The plane of each individual coil 10 is oriented generally transversely with respect to the circular field lines generated by axially extending defects, such as the circular field lines in FIGS. 13-15. Thus the changing magnetic flux linking each coil will be detected by coils 10a and 10b.

The detector or pickup coil 10 comprises a pair of vertical coils 10a and 10b. In the preferred embodiment of this invention, each of the detector coils 10a and 10b has a sinusoidal distribution of detecting coil conductors. The conductor distribution of one sinusoidal coil is displaced relative to the other sinusoidal coil so that there is a phase displacement between conductor distributions. In the preferred embodiment of this invention, this phase displacement is equal to 90° so that one detector coil 10a can be referred to as the sine detector coil while the other detector coil 10b can be referred to as the cosine detector coil. Of course the circular driven field lines, as represented in FIGS. 13-15, would differ in intensity at different angular positions depending upon the location of the axial defect $D_2$ relative to the driving magnetic field produced by coils 32a and 32b. If the defect occurred in the vicinity of a portion of the cosine coil having a large distribution of conductors, the signal generated in the cosine coil would be significantly larger than the signal generated in the sine coil, because the sine coil would have a correspondingly smaller electrical conductor distribution in the vicinity of the axial defect. Since the distribution of conductors at different positions in the two coils is known, appropriate gain factors can be used to adjust the combination of signals in the two separate detector coils 10a and 10b, so that the resultant signal reflects both the size and location of the axial defect.

Figure 10:
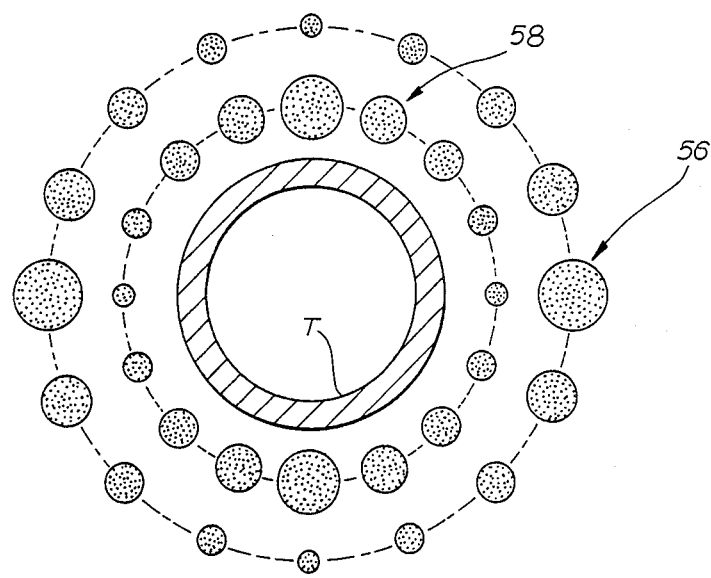
FIG. 10 is a cross-sectional schematic showing the sinusoidal distribution of sine and cosine windings relative to the tubular element.

In the embodiment of FIG. 2, the construction of the transverse AC drive coils 32 and the AC detection coils 10 is similar. Each coil comprises two component sinusoidal coils distributed around the circumference of the detection head 4. The relative sinusoidal distributions 56 and 58 are shown in FIG. 10. The detector coils 10 are located on the interior of the detection head and are spaced from the tubular element moving therethrough. The two AC drive coils 32 encompass the detector coils 10 and are positioned around the exterior of the detector head assembly. Coils 32 are vertically wound in the same manner as the detector coils 10. The sinusoidal distribution contributing to the fluctuating field is, however, almost entirely due to the sinusoidal distribution of conductors along the inner portion 32' of the outer drive coil. The outer vertical section 32A" is sufficiently spaced from the tubular member T, in relation to inner coil 32', that the contribution of the outer vertical conductors 32" can be ignored.

The drive coils 33 in FIG. 4 also have two sinusoidal conductor distributions for generating the constant rotating transverse magnetizing field in the same manner as the coils in FIG. 2. However, all of the conductors comprising the drive coil 33 are at substantially the same radial distance from the tubular element T. The drive coils 33 of FIG. 4 are constructed such that an individual conductor extending in one direction at a first circumferential position will extend in the opposite direction at a position 180° from the first circumferential position. The conductors thus extend upwardly, then around a semicircular portion of the detector head, then down at an opposed position on the detector head and thence around at least a portion of the detector head at a second axially spaced position. The conductors can thus be wound in a generally sinusoidal configuration. The drive coil configuration of FIG. 4 is substantially more efficient in terms of the power required to generate a magnetic field of a given intensity. Essentially half the number of conductors are needed to construct the drive coils 33 as would be needed to construct the drive coils 32. Either configuration could, however, be used to generate the transverse magnetic field needed for axial defect detection. It should be remembered that the transverse magnetic field can be of much smaller intensity than the longitudinal uniform DC saturating magnetizing field. Therefore, the relative inefficiency of the drive coil configuration of FIG. 2 in comparison to the configuration of drive coils 33 in FIG. 4 may be obviated by other considerations.

The driven fields induced by the fluctuating magnetizing field can be detected by detecting means located around the periphery of the tubular element T. In the preferred embodiment, detector coils 10 are positioned radially between the AC drive coils 32 and the tubular element T. In the preferred embodiment of this invention, the AC detecting coils 10a and 10b extend longitudinally over a portion of the tubular element T which is greater than the diameter of the tubular element. Thus a defect $D_2$, which is longer than the diameter of the tubular element, will create a signal of sufficient intensity to be detected by coils 10a and 10b. The axial extent of the coil determines the size of the detectable defect.

In the preferred embodiment of this invention, the detecting coils 10a and 10b are radially spaced from the outer surface of the tubular element T. Although the tubular element T will, in general, be centered relative to the detecting head 4, axial movement of the tubular element relative to the detecting head 4 will inevitably result in lateral movement of off-centering of the tubular element T relative to the coils 10. Such off-centering will result in some change in the signals generated in detecting coils 10. In the preferred embodiment of this invention, the plane of the detecting coils 10 is substantially vertical and will therefore be perpendicular to the generally circular differential field lines as indicated in FIGS. 13-15. The coils are thus ideally oriented to detect differences in the magnetic field as a result of fluctuations due to the passage of defects in the tubular element T. The sinusoidal distribution provides some degree of off-centering compensation due to the variable position of tubular elements T.

The two detecting coils 10a and 10b comprise sinusoidal coil windings similar in construction to the drive coil line 32 shown in FIG. 2. Since the coils 10 extend completely around the circumference of tubular element T, a defect at any circumferential location will generate signals in both of the sinusoidal detecting coils 10a and 10b. Since the conductor distribution, and hence current, in each of the coils varies angularly around the tubular element T, the disturbed or differential field will produce a different signal in the coils at different angular positions.

The eddy current and flux leakage effect sensed by the detector coils 10a and 10b are manifested by amplitude changes and by phase changes. For example, the phase of the eddy current is 90° out of phase with the field generated by the driving coils 32. Clearly then eddy current effects will result in a phase change of the detected signal with respect to the driving signal. In the preferred embodiment of this invention, this change in phase is detected to measure the size of axially or longitudinally occurring defects, such as defects due to rod wear interference, which have a length generally greater than the diameter of the tubular element 2.

Combined analog and digital signal processing can be employed to obtain the magnitude of signals produced in both the sine detecting coil 10a and the cosine detecting coil 10b. However, in order to determine if the signals produced in both coils are due to a defect in a tubular element or are due to some other disturbance, such as uniform wall loss, some means of determining the angular variation of the signals must be employed.

Figure 20:
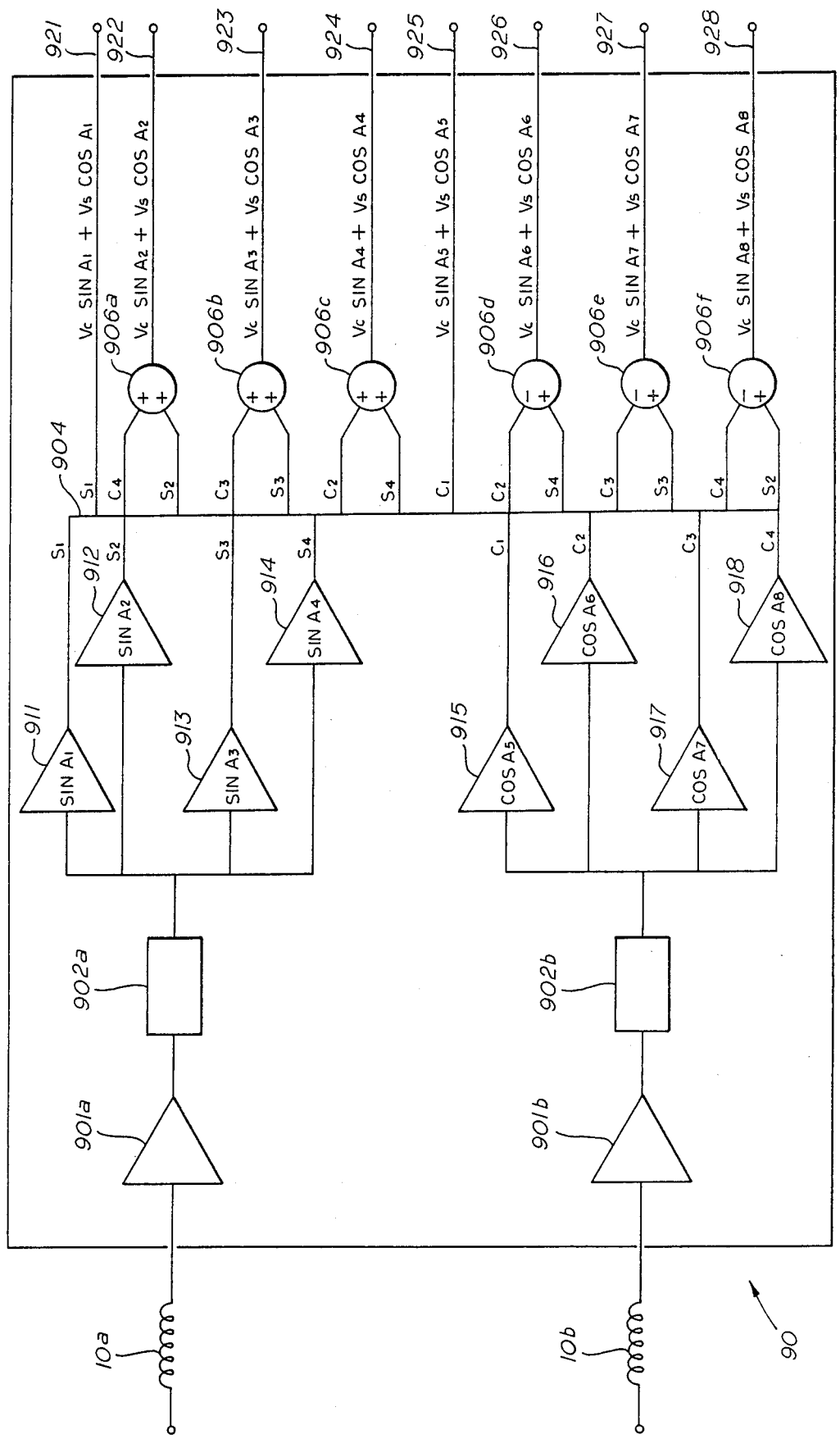
FIG. 20 is a diagram of the multi-channel detector component for rod wear detection.
Figure 21:
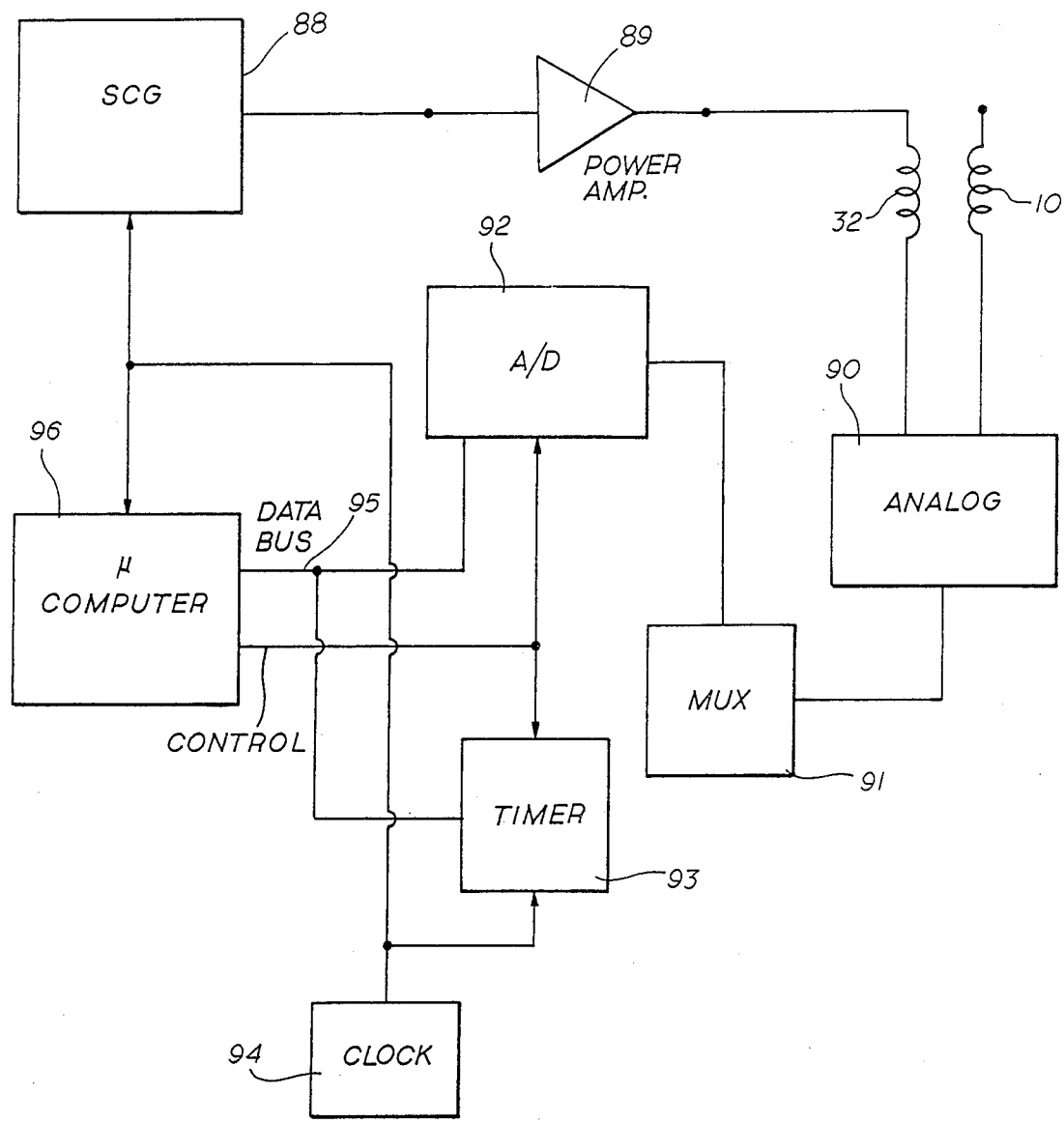
FIG. 21 is a diagram of the rod wear signal processing.
Figure 19:
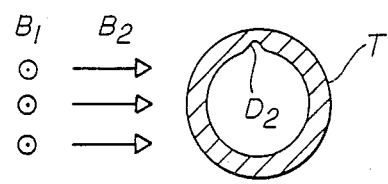

The computer controlled rod wear signal processing is depicted in FIGS. 20 and 21. Both the excitation of magnetic fields in the tubular elements and the detection of the effects due to axial defects, such as wear due to sucker rod interference, are responsive to a single clock signal 94. A sine cosine wave generator 88 responsive to clock 94 is used to synchronously generate the sine and cosine waves used for the exitation of driving coils 32a and 32b. The sine cosine generator 88 in the preferred embodiment of this invention is a digital generator of conventional construction. Sine cosine generator 88 contains appropriate control electronics and filters and a read only memory (ROM) containing the sine and cosine functions. The analog sine and cosine electronic waves generated by sine cosine generator 88 are amplified by a conventional power amplifier 89 in order to provide sufficient electrical power to the driving coils 32a and 32b (see FIG. 2) to generate fluctuating magnetic fields of appropriate intensity. In FIG. 21, the driving coil 32 is intended to represent both the sine and cosine driving coils 32a and 32b. The magnetic field induced in the tubular elements T positioned in the center of both the driving coils 32 and the pickup coils 10 (see FIG. 3) is detectable in coils 10 in the form of an induced signal voltage which comprises analog signal as previously described. Again, coil 10 represents the two sine and cosine detecting coils 10a and 10b and two signals are transmitted from pickup coils 10 to a multi-channel detector component 90.

The multi-channel detector component 90 shown in greater detail in FIG. 20 generates a plurality of directionally dependent signals derived from the input from both the sine and cosine coils 10a and 10b. The signals from sine and cosine coils 10a and 10b are initially amplified by conventional amplifiers 901a and 901b having appropriate constant gain factors. The amplified signals then pass through band pass filters 902a and 902b to remove extraneous signals. Signals from band pass filters 902a and 902b are then fed into a plurality of separate amplifiers 911-918, each of which has a gain factor corresponding to the magnitude of either the sine or cosine of predetermined angles A1-A8. The output of amplifiers 911-918 are designated S1-S4 corresponding to the sines of angles A1-A4 and C1-C4 corresponding to cosines of angles A5-A8. In the preferred embodiment of this invention, the gain factors of amplifiers 911-918 correspond to the magnitude of the sine and cosine of angles equally spaced between zero and 90°. These gain factors are related to the angular variation of the conductor distribution in the sinusoidal detector coils. The output signals S1-S4 and C1-C4 from amplifiers 911-918 are then fed along conductors, represented by a single bus 904, and voltage signals corresponding to sine and cosine of equal angles are combined to generate outputs 921-928 in eight channels, each corresponding to an angle between zero and 180°. Since the sign of the sine and cosine of the angles involved has been neglected in amplifiers 911-918, the appropriate sign is introduced as part of the summation at 906A-906F. Note that the output at channel 925 corresponds to an angle of 0° and its sine would be equal to zero. Therefore, no summation is necessary along line A5. Similarly, line A1 corresponds to an angle of 90° since the cosine 90° would be zero. In the preferred embodiment of this invention, eight separate signals corresponding to eight equally spaced angles are output from multi-channel detector component 90. Although eight channels have been found to provide sufficient circumferential coverage for a tubular member travelling at velocities corresponding to conventional tubing retrieval operations, a different number of channels could be selected without departing from the invention as described herein. In the preferred embodiment of this invention, the voltage in each channel is obtained according to the following formula:

$$V_{channel} = V_s \text{ Sin Angle} + V_c \text{ Cos Angle};$$

where $V_s$ is equal to the voltage obtained in one of the detector coils 10a which can be referred to as the sine coil and $V_c$ is equal to the voltage in coil 10b which can be referred to the cosine coil. FIG. 21 shows the eight separate channels output from multi-channel detector component 90 to a conventional multiplexor 91.

The analog signals from conventional multiplexor 91 are next directed to a conventional analog to digital converter 92. The analog to digital converter 92 is responsive to a timing signal conventionally generated by timer 93, responsive to clock 94, to sample the value of the digitized analog signal at regularly spaced intervals. In the preferred embodiment of this invention, the regularly spaced intervals can correspond to intervals of less than 50 microseconds. Intervals of this magnitude are necessary because of the multiple signals corresponding to the multiple channels which must be sampled, and because a certain sampling rate must be maintained to permit the detection of rod wear signals in a moving tubular element, the velocity of which is dictated by standard tubing retrieval operations. Microcomputer 96, which controls both the sine cosine wave generation and which performs the computation necessary to correlate the signals detected in pickup coils 10 with the extent of sucker rod wear, controls the timer 93 and the analog to digital converter 92. This control permits the computer to determine when the analog signals in each channel output from multi-channel signal detection component 90 are equal to zero. In this invention, the microcomputer 96 stores sequential values of the voltage signal and time information for each channel in an appropriate memory. The signals are output from analog to digital converter 92 along data bus 95 to the computer. These sequential values are obtained at the regularly spaced intervals derived from timer 93 responsive to clock 94. In order to determine the time at which the individual channel signals equal zero, the microcomputer detects a change in sign between successive values of the signal voltage output by analog to digital converter 92. When the microcomputer 96 detects a change in sign, the microcomputer 96 performs an interpolation between the two successive sampling times, corresponding to known times and intervals responsive to clock 94 and timer 93. Since the value of the voltage signals output from the analog to digital converter 92 are maintained in the memory of microcomputer 96, an interpolation routine over the prescribed time interval will determine the time at which each signal is equal to zero. Thus the zero crossing for each channel will be determined. This zero crossing time will next be compared to the time at which wave forms generated in the sine cosine generator 88 were equal to a specified reference value. The time interval between the reference value time for the excitation or driving wave forms can then be compared with the zero crossing of each channel signal. This time delay will be equal to the sum of the time delay due to the system components and the time delay due to the intensity of the induced magnetic field in the inspected tubular element. Since the time delay of the components can be expected to remain constant, any change in the time delay is due entirely to changes in the character of the tubular element. Thus sucker rod wear defects will result in a detectable signal and in a change in the time interval. In this manner, the phase change resulting from sucker rod wear defects can be detected and used as a measure of the extent of sucker rod wear. In the preferred embodiment of this invention, the phase change due to rod wear can be expected to be on the order of 0.6° maximum. Gradation of detectable rod wear will therefore require resolution of phase shifts of less than 0.6°, thus requiring an especially accurate method for detecting the time delay.

Velocity and Position Detector

Figure 22:
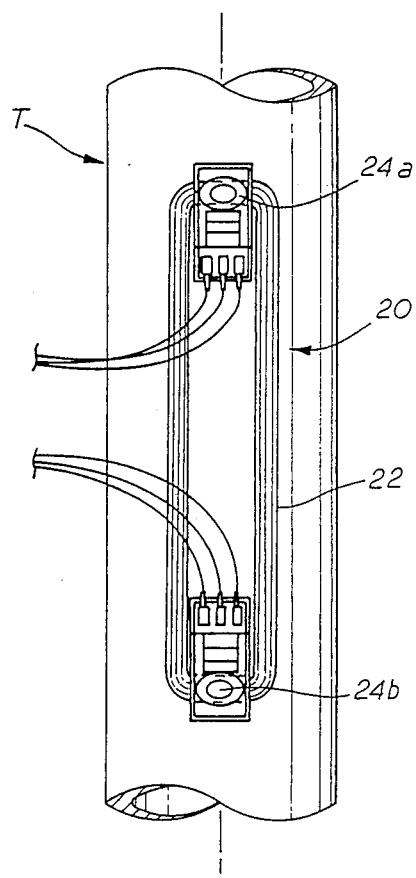
FIG. 22 is a view of a velocity detector mountable on the tubing trip tool head.
Figure 23:
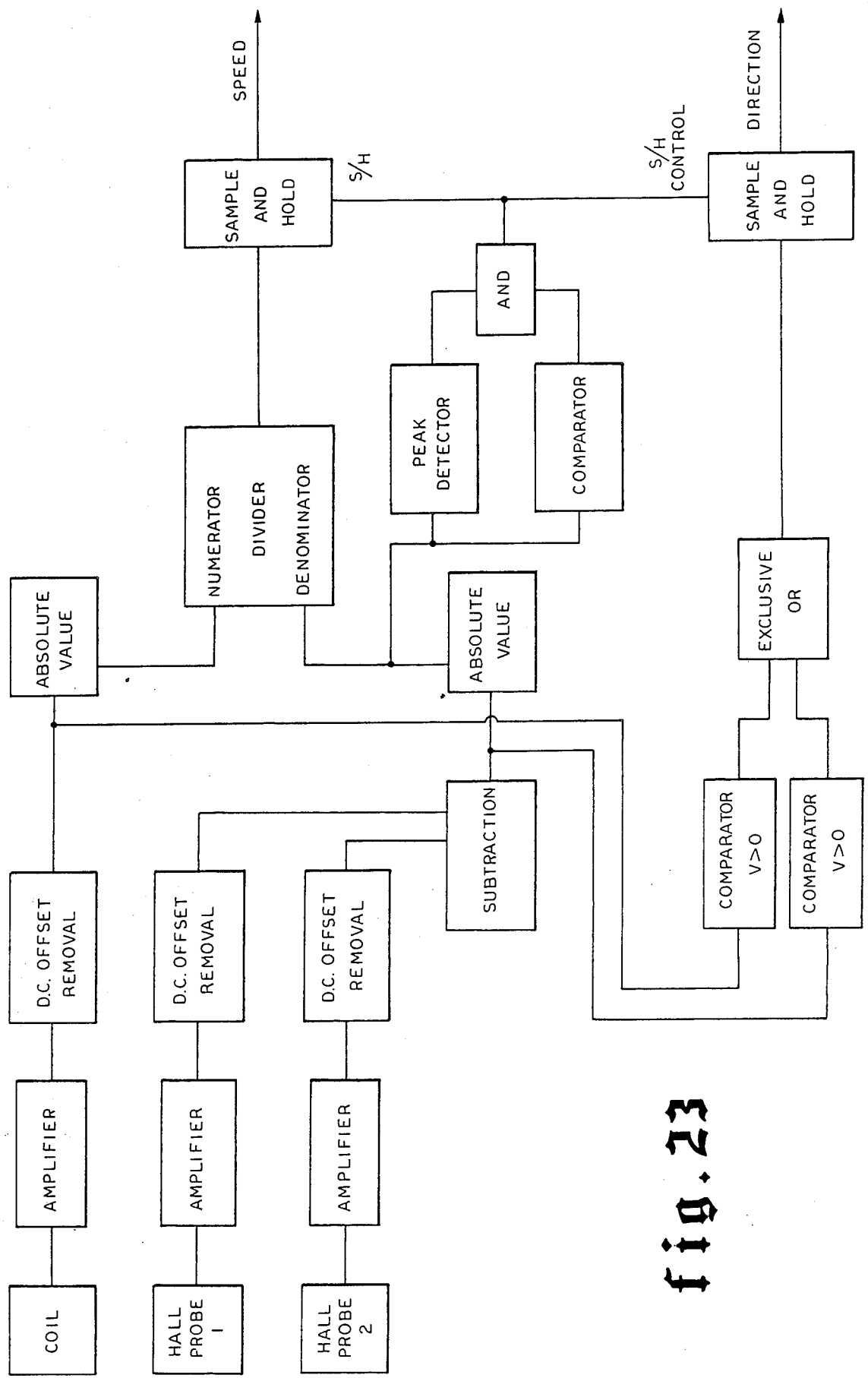
FIG. 23 is a diagram of the signal processing for the velocity detector.

The cross-sectional area of a moving tubular element, the depth of local defects, such as corrosion pitting defects, and the size of longitudinally extending defects, such as defects due to sucker rod interference, can be determined by detector 4 independent of the velocity of the tubular element T relative to the detector. There may also be a need to determine the velocity of the tubular element T relative to the tubing trip tool 2. For example, it may be necessary to not only determine the existence and size of a defect in a particular tubing section of tubular string T, but it may be necessary to determine the position of the defect in both the tubing string and in the constituent tubular section. A noncontact velocity detector 20 is shown positioned on the tubing trip tool head 4 in FIG. 2. The preferred embodiment of each velocity detector used in this invention comprises two detector elements 24a and 24b in which a signal is produced by the magnetic field. In the preferred embodiment of this invention, detector elements 24a and 24b comprise elements in which the voltage is generated due to the Hall effect. These Hall probes 24a and 24b are then incorporated into a velocity detector coil 22 as shown schematically in FIG. 22. The signal produced in the coil is related to both the velocity and the magnetic field sensed by the coil. The signal in the coil is proportional to the vector cross product of the velocity and the magnetic field whereas the signals in the Hall probes are due solely to the magnetic field. The output voltage of a pickup coil near a changing magnetic field is proportional to the rate of change of the field of fixed spatial orientation passing by the coil, then any output voltage is proportional to the product of the field strength and the field velocity.

The changing magnetic fields due to the velocity of the tubular element T are the magnetic leakage fields emanating from the pipe either as pitting signals, as signals due to average wall changes, or as pipe noise. For example, a leakage field is created by permeability fluctuations within the ferromagnetic tubular element T. In the preferred embodiment of each velocity detector, the two Hall probes 24a and 24b are incorporated into the coil 22 with the Hall probes oriented to detect radial changes in the leakage fields. When the coil and Hall probes are oriented as shown in FIG. 2, the coil voltage is equal to the product of the number of turns in the coil, the velocity of the tubular element, the width of the coil, and the difference between the radial components of the magnetic leakage field at the two ends of the coil. The voltage of each Hall probe is equal to the gain of the Hall probe device times the radial component of the leakage field of the Hall probe. The ratio of the coil voltage to the difference in the voltage between the two Hall probes thus determines the pipe velocity.

Figure 24:
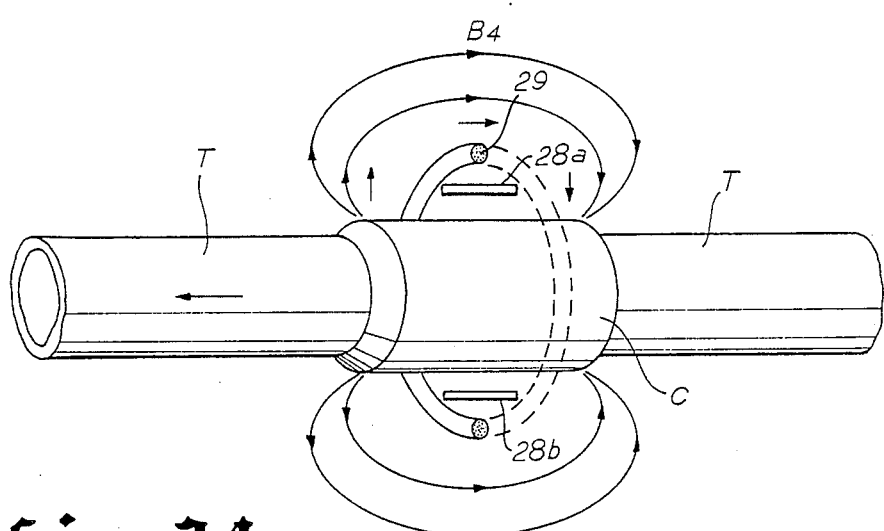
FIG. 24 is a view of the end coupling detector.

A block diagram of analog electronics which could be used to measure the velocity of a tubular element is shown in FIG. 24. The absolute values of the signals must be used to accomodate the divider. A sample and hold detector is used to eliminate the erroneous measurements that occur when the denominator is small or rapidly changing. It is operated such that the velocity is updated only when the Hall probe difference is at a peak and within a reasonable voltage range. The direction of motion is determined by correlating the polarity of the coil signal and the Hall probe difference. It will be understood, of course, that other conventional circuits could be used to determine the velocity measurement.

The velocity detector employed in the tubing trip tool head 4 is located on the exterior of the detector coils 10. The velocity detector can be spaced from the surface of the ferromagnetic tubular element T and need not be in contact with the tubular element. The detector is insensitive to radial position, applied field, signal amplitude and pipe grade. This noncontact velocity measurement is especially useful in conjunction with removal or insertion of the tubing string T from an oil or gas well. In the preferred embodiment of this invention, this velocity measurement permits the operator to determine the axial position along the tubular element and along each individual tubing section.

END COUPLING DETECTOR

The noncontact velocity detector described herein can be used to determine the axial position of a defect in an inspected tubular member. Knowledge of the defect location in specific tubular sections forming the tubing string is important, and knowledge of the defect location in the tubing string is also significant in that such knowledge would permit the operator to determine the exact location in the well at which wall thickness reduction, corrosion pitting or wear due to sucker rod interference is a problem. Such knowledge would permit construction of a string profile to determine significant problem areas.

In order to construct a string profile and to accurately obtain information as to the location of defects in any particular tubular string, the position of the tubing string relative to the well head must be determined. In the preferred embodiment of this invention, the location of the tubing string is determined by use of the noncontact velocity detector and by use of a noncontact end coupling detector. For conventional tubular strings, such as casing, production tubing and completion strings used in oil and gas wells, the individual sections are joined by end couplings.

There are two common types of end couplings. The first consists of a collar having internal threads on both ends which is used to join two lengths of casing, tubing or conduit. The cross-sectional area of the separate coupling member and the end portions of the tubing sections engaging the separate member will be greater than the cross-sectional area of the tubular section intermediate its ends. A second type of end coupling comprises an upset section on the ends of adjacent tubing sections. The ends of adjacent tubing sections have mating threads in the vicinity of the upset ends, and the tubular sections are joined directly without the necessity of employing a separate coupling section or collar. These directly engagable tubular sections are, however, upset, with the portion of the tubing section in which threads are machined being thicker than the remaining portion of the tubing section. Thus the cross-sectional area in the vicinity of the end coupling is greater than the cross-sectional area of the tubing intermediate its ends whether a separate collar is used or whether interengagable mating threads are employed on adjacent tubular sections.

Figure 25:
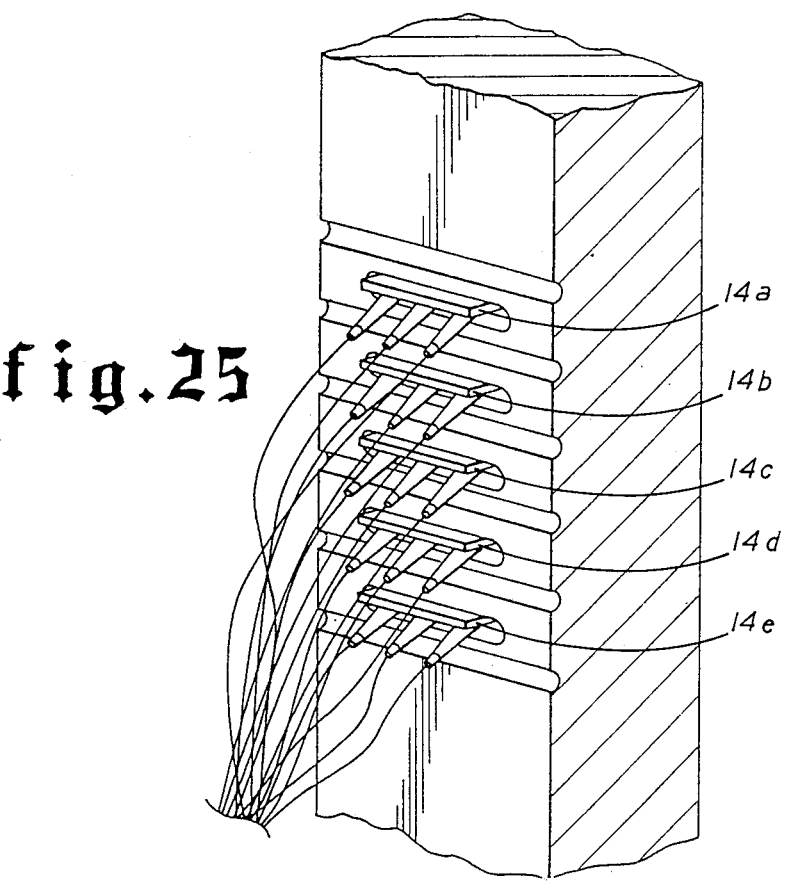
FIG. 25 is a view of the mounting of detector elements for measuring local defects in the detector head.

The exact location of each tubing section, and thus the location within the tubular string can be determined by detecting both the presence and the direction of movement of each end coupling. In the preferred embodiment of this invention, a magnetic field having a uniform strength and fixed relative to the well head is applied to the portion of the tubular string and tubular sections in the vicinity of the well head. An induced magnetic field in the tubular section results. FIG. 25 shows tubing sections T interconnected by end coupling C and the lines of magnetic flux representing the induced magnetic field B4 in the area of end coupling C. Since the cross-sectional area at end coupling C is greater than the cross-sectional area of tubing T, the strength of the magnetic field B4 in the vicinity of the end coupling will be greater than the strength of the magnetic field induced in the tubular section intermediate its ends. If the strength of the magnetic field B4 detected at the well head is greater than a predetermined reference value in excess of the field strength normally induced in a tubing section having a constant cross-sectional area intermediate its ends, the presence of a coupling can be distinguished from normal variations in the strength of the induced magnetic field in the tubing section. In the preferred embodiment of this invention, the strength of the reference signal or the threshold value of the magnitude of the induced magnetic field would be less than the magnitude of a magnetic field normally induced by an end coupling of known dimensions to account for slight variations of the magnetic field induced in the coupling.

In normal drilling, production and completion operations, the tubular sections comprising the tubular string are intermittently lowered and raised during either insertion or removal into or from the well. Therefore simple detection of the presence of an end coupling in the vicinity of the well head will not be sufficient to identify specific tubular sections comprising the tubular string or to identify the location of a tubular section within the tubular string. Therefore it will be necessary to identify the direction in which the coupling moves with relation to the well head. By identifying both the presence of the coupling at the well head and the direction of movement of the coupling with respect to the well head, each instance in which the coupling passes the well head in either direction can be stored in a conventional memory, and conventional computing means can be provided to tabulate the number and location of each end coupling encountered during insertion or removal of the tubular string into or from the well.

In the preferred embodiment of this invention, each end coupling, and its direction of movement are detected and counted by first magnetically detecting the presence of an end coupling having an enlarged cross-sectional area in the manner previously described. One or more detectors capable of generating signals of opposite signs corresponding to movement of the tubular strings T and end coupling C in opposite directions relative to the detector are employed to determine the direction of movement of an end coupling C. In the preferred embodiment of this invention, an encircling coil 29 similar to encircling pickup coil 30, which is used to determine the average wall thickness of the tubular section, is employed to detect an end coupling C having a greater thickness than the tubular section. Encircling coil 29 functions in the same manner as coil 30 as previously described with respect to measurement of the wall thickness. Indeed an apparatus in accordance with this invention could employ the same encircling coil, both for the wall thickness measurement of the tubular string T and to detect the presence of an enlarged end coupling C.

Once the presence of the end coupling has been detected by encircling coil 29, the direction of movement can be detected by separate detectors, such as detectors 28a and 28b. In the preferred embodiment of this invention, detectors 28a and 28b comprise Hall probes which generate a voltage proportional to the product of the input current, the magnetic flux density, and the sine of the angle between the magnetic flux density and the plane of the Hall generator. These elements are similar to the elements used for corrosion pitting detection and the voltage is produced in response to the electromagnetic phenomenon generally referred to as the Hall effect. The sign of the output voltage of Hall probes 28a and 28b will be opposite when subjected to magnetic lines of force in a magnetic field extending in opposite directions. As shown in FIG. 25, in which the direction of movement of the tubular string T is in the direction of the arrow, the magnetic lines of force of magnetic field 4 extend in the directions shown. Magnetic lines of force for the end coupling C increase in intensity as the end coupling C moves into an applied magnetic field when the magnetic lines of force extend outward as shown. At the trailing edge of the end coupling C, the magnetic lines of force in the induced magnetic field B4 extend inwardly toward the tubular string T and end coupling C as shown schematically in FIG. 25. Thus the Hall probes 28a and 28b will be subjected to magnetic lines of force or flux extending in opposite directions during passage of end coupling C through the applied magnetic field. When the Hall probes 28a and 28b are positioned near the leading edge of the moving end coupling C, the magnetic lines of force will extend radially outward. When the Hall probes 28a and 28b are adjacent the trailing edge of the end coupling C, they will be subjected to magnetic line of forces extending inwardly toward end coupling C. Thus the voltage generated by Hall probes 28a and 28b in the vicinity of the leading edge of end coupling C will have the opposite sign from the voltage generated when the Hall probes 28a and 28b are in the vicinity of the trailing edge of end coupling C. One sequence of the signs of the voltage generated by Hall probes 28a and 28b will correspond to movement of the tubing string T and end coupling C in the direction shown in FIG. 24. Movement of the tubing string T and the end coupling C in the opposite direction will result in an opposite sequence for the signs of the voltage generated by the Hall probes 28a and 28b. Thus the direction of movement of end coupling C through the applied magnetic field can be recognized by conventional computing means and specific tubular sections can be located.

When used in conjunction with a position indicator, such as would be provided by a device capable of measuring the velocity of the tubing string T, a profile of defects, including average wall thickness reduction, corrosion pitting, and wear due to sucker rod interference, can be tabulated as a function of the position of the tubular string in the well. Such information can give the operator valuable insights on the phenomenon being encountered within an subterranean oil or gas well. Furthermore, the use of the end coupling detector and the velocity detector described in the preferred embodiment of this invention will permit an accurate tabulation of defects in individual used tubing sections, to permit the operator to determine if such tubing sections should be replaced.

EXPANDABLE HEAD

Figure 26:
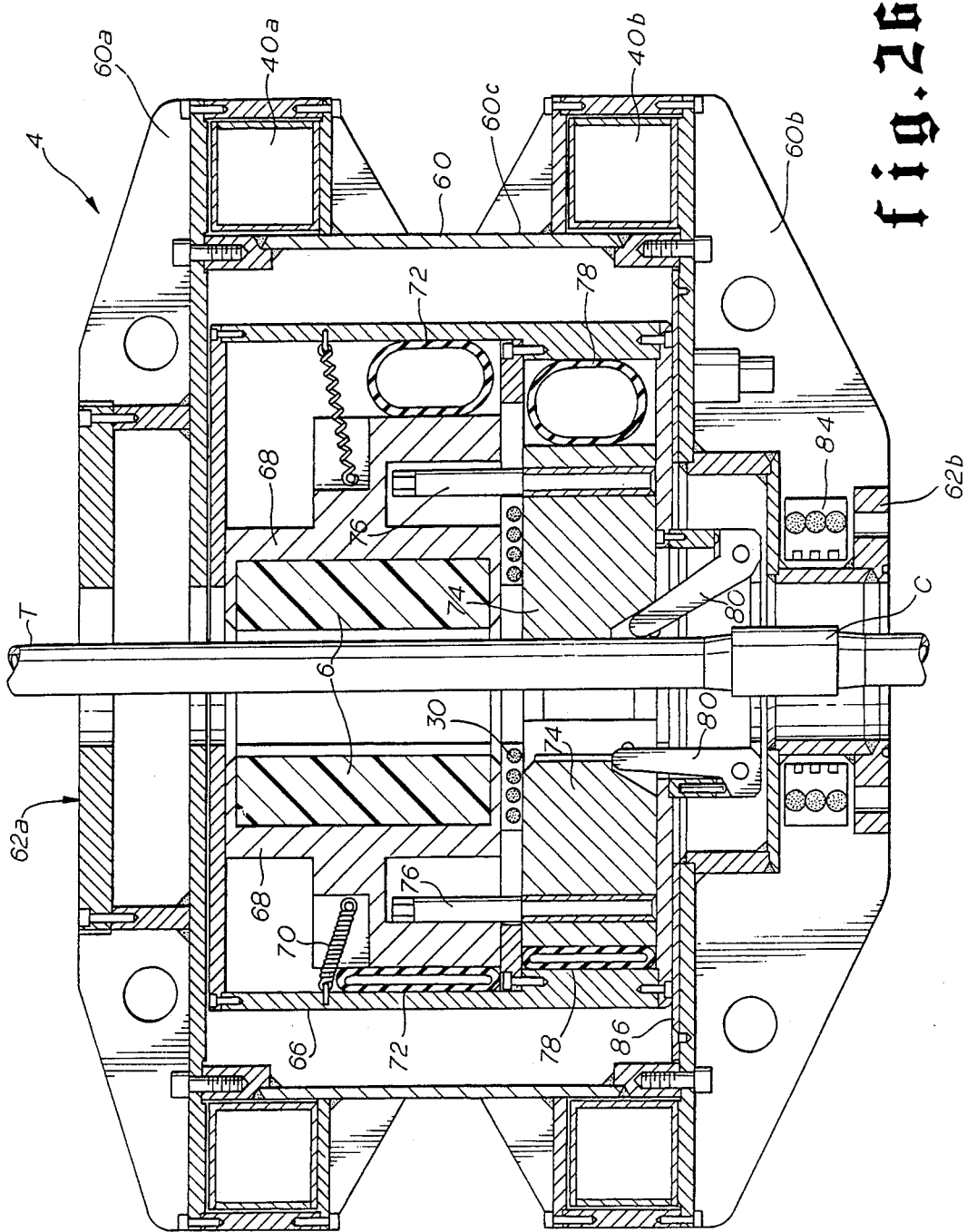
FIG. 26 is a view of the expandable detector head used at the well head.

FIG. 26 is a longitudinal sectional view of one version of an expandable tubing trip tool 4. The expandable head shown therein can be positioned below the rig floor and provides central clearance for oil field tubing T or any object passing through up to well bore size. FIG. 26 illustrates the expandable head comprising the preferred embodiment of this invention in two different positions. The portion of the tool to the right of the tubing T in FIG. 26 depicts the tool in its innermost measuring position. The portion of the tool located to the left of the tubing T in FIG. 26 depicts the tool with the detecting elements shifted to an outermost position to provide clearance for obstructions in the tubing string up to well bore size, such as packers or tubing anchors. It should be understood that both the right and left portions of the tool comprising the preferred embodiment of this invention are radially shiftable in unison, and separate elements of the tool do not occupy the separate positions shown in FIG. 26. Two opposite elements of the tool are merely shown in the configuration of FIG. 26 for the purpose of explaining and comparing the open and closed modes of operation of the tool.

An outer cylindrical housing 60 comprising upper and lower sections 60a and 60b and cylindrical section 60c provides mounting plate for slips 62a and flange 62b for mounting the expandable head on the blowout preventors. It should be understood that the expandable head shown in FIG. 26 is comprised of a plurality of radial segments, each of which is adapted to shift inwardly and outwardly in unison with the other segments. FIG. 2 discloses a four segment expandable head containing the same essential elements as FIG. 26. A central opening provides clearance through the tool to pass the tubing and any obstructions carried therethrough. A floating detector cage 66 is positioned on the interior of outer tool housing 60. Floating detector cage 66 is not fixed relative to the outer housing 60 and is free to move radially. In the preferred embodiment of this invention, the lower surface of cage 66 rests on a low friction sliding surface 86 which is mounted on the lower portion 60b of the outer tool housing.

A plurality of arcuately shaped detector mounting blocks 68 are positioned within the upper portion of the detector cage 66. Each of the detector mounting blocks contains at least one of the arucate detector segment 8 which, in the preferred embodiment, includes the transverse magnetic field detecting elements 10, the flux leakage detecting elements 14, and the velocity detecting elements 20. The construction of the elements in the detector housing of the embodiment of FIG. 26 is shown in greater detail in FIG. 2 and FIG. 3.

Each detector mounting block 68 is attached to the detector cage 66 by means of a coil spring 70 which biases the detector block 68 outwardly relative to the centrally disposed tubing. A continuous inflatable detector air bag 72 displaces each mounting block 68 to the innermost position to locate the detector head in the inner measuring position as shown in the right hand portion of FIG. 26. Air bags 72 are connected to an appropriate source of compressed air. A fast acting valve of conventional construction can also be positioned in communication with air bag 72 so that outward movement of connector blocks 68, tending to deflate the air bags, can be accomplished by venting the air within the air bags through the conventional valve.

Centering blocks 74 are located below the detector blocks 68. Tthese centering blocks 74 comprise arcuately shaped mounting members which, in the innermost position as shown in the right hand side of FIG. 26, engage the exterior of the tubing T to center the detector element with respect to the tubing. Note that in the preferred embodiment of this invention, the centering blocks are in engagement with the tubing T but the detecting elements 8 are spaced slightly from the periphery of the tubing T when an inner measuring position as shown in the right hand portion of FIG. 26. In the preferred embodiment of this invention, the spacing between the periphery of the tubing element and the detector element is approximately two-thirds of one inch. As shown in the left hand portion of FIG. 26, the centering blocks 74 are radially shiftable to open up to well bore size and provide clearance so that obstructions affixed to the tubing, such as packers, tubing anchors, etc., can move therethrough. In the normal operating mode, each coupling passing through will force the centering blocks radially outward while maintaining centering with respect to the tubing, but without radially displacing the head.

Each centering block 74 has an upstanding pin 76 received within a companion slot within the mounting block 68. Movement of the centering block away from the tubing string to an extent greater than required to pass a coupling brings the corresponding pin 76 into engagement with the detector mounting block 68, as shown in the left hand portion of FIG. 26, to move it radially outward. Centering blocks 74 are also biased radially outward by springs (not shown) and are displaced inward by air bag 78. In the preferred embodiment of this invention, air bag 78 acts in virtually identical fashion to air bag 72, although air bags 72 and 78 are separate structures. Each communicates with a source compressed air but neither air bag communicates directly with the other air bag.

In addition to the centering blocks 74, four equally spaced fingers 80 located at the lower portion of the expandable head are also positioned to contact the tubing T. Fingers 80 also engage a mating inclined surface on centering block 74. When an unexpected obstruction on tubing T engages fingers 80, the fingers will act to push the centering block 74 radially outward thus moving detector mounting blocks 68 out of the way to prevent damage during passage of the obstruction. The passing through of a coupling, however, will not effect radial movement of the detector mounting blocks. Outward movement of the centering blocks 74 and detectormounting blocks 68 can also be provided by a command signal when movement of an obstruction, larger than coupling C, such as a packer or other well tool, is anticipated. In other words, the detecting elements are selectively expandable and are expanded only upon movement of an obstruction or component of the tubing string past the detecting elements in either direction. Such movement will occur by deflating air bags 72 and 78 on signal to permit springs 70 to shift the mounting block and the centering blocks outwardly to clear the obstruction.

An automatically triggered signal indicating that an obstruction larger than a coupling is present may also be obtained from coupling detectors 84 mounted on lower mounting housing section 60b. These coupling detectors can comprise a DC drive coil having sufficient amp turns to saturate the tubing adjacent thereto with encircling detector coils for determining changes in the total magnetic flux to indicate that an obstruction substantially larger than a coupling is approaching the expandable detector head.

In addition to the detector elements located in detector mounting blocks 68, the expandable head shown in FIG. 26 also includes both DC and AC drive coils. The AC drive coils used in the expandable head are positioned in the detector head element. The construction of the AC drive coils used in such expandable heads correspond generally to the configuration of the AC drive coils 32 shown in FIG. 2. DC drive coils containing a sufficient number of amp turns to saturate the tubing T are mounted on the exterior or interior of the expandable head. These drive coils 40a and 40b are positioned such that a uniform longitudinal saturated magnetic field can be induced in the tubing T in the vicinity of the detector head. The expandable head depicted herein can also be constructed utilizing a single DC drive coil 40.

Although the invention has been described in terms of the specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A method of determining the extent of defects in a ferromagnetic element during axial movement of the ferromagnetic element, comprising the steps of:
   applying a first magnetic field to the ferromagnetic element of sufficient intensity to establish a uniform magnetic property in the portion of the ferromagnetic element passing through the first magnetic field;
   detecting a change in a signal produced by the uniform magnetic property in the ferromagnetic element functionally related to the cross-sectional area along the axis of the ferromagnetic element and at least substantially functionally independent of axial movement of the ferromagnetic element to detect a cross-sectional area defect in the element;
   detecting a change in relative values of two derivatives, each of a different order, of an axial component of the uniform magnetic property as altered by the defects to measure the depth of defects in the ferromagnetic element;
   applying an second fluctuating magnetic field to the ferromagnetic element in addition to the first magnetic field; and
   detecting driven fields induced in the ferromagnetic element by the fluctuating magnetic field and comparing the driven fields to the fluctuating magnetic field to detect axially extending defects in the ferromagnetic element.

2. A method of determining the extent of defects in a ferromagnetic element during axial movment of the ferromagnetic element, comprising the steps of:
   applying a saturating magnetic field to the ferromagnetic element of a sufficient intensity to produce a saturated magnetic field in the portion of the ferromagnetic element passing through the magnetic saturating field;
   detecting a change in the total magnetic flux generated by the saturated magnetic field in the ferromagnetic element to detect a cross-sectional area defect in the ferromagnetic element;

comparing two non-zero derivatives of different orders of an axial component of flux leakage in the saturated magnetic field to detect a change in flux leakage in the saturated magnetic field as altered by the defects and thereby measure the depth of local defects in the ferromagnetic element;

applying a fluctuating magnetic field to the ferromagnetic element in addition to the saturating magnetic field; and detecting driven fields induced in the ferromagnetic element by the fluctuating magnetic field and comparing the driven fields to the fluctuating magnetic field to detect axially extending defects located at discrete lateral locations relative to the axis of and in the ferromagnetic element.

3. The method of claim 2 comprising the further step of recording defects as a function of their axial position in the ferromagnetic element.

4. The method of claim 3 comprising the further steps of measuring the velocity of the ferromagnetic element by detecting, at a location fixed relative to the saturating magnetic field, a first signal dependent upon the velocity of the element relative to the saturating magnetic field and upon a magnetic leakage field, detecting a second signal dependent upon the magnetic leakage field and independent of the velocity of the element, and comparing the first signal to the second signal to measure the velocity of the ferromagnetic element.

5. The method of claim 2 wherein the saturating magnetic field induces a saturation value of magnetic flux extending axially in the portion of the ferromagnetic element extending through the saturating magnetic field.

6. The method of claim 2 wherein the depth of local defects is determined by signal processing employing a plurality of detectors selectively spaced geometrically relative to the ferromagnetic element to detect the change in flux leakage.

7. The method of claim 2 wherein the step of detecting a change in flux leakage to measure the depth of local defects comprises measuring multiple local defects having irregular lengths and widths.

8. The method of claim 2 wherein the step of detecting a change in flux leakage to measure the depth of local defects comprises positioning a plurality of axially spaced voltage generating flux leakage detection elements around the ferromagnetic element to determine the shape of the leakage field.

9. The method of claim 2 wherein the fluctuating magnetic field comprises a cyclically fluctuating magnetic field.

10. The method of claim 9 wherein the fluctuating magnetic field rotates around the axially moving ferromagnetic element.

11. The method of claim 10 wherein rotation of the fluctuating magnetic field is induced by current changes in fixed electrical conductors distributed around the ferromagnetic element.

12. The method of claim 2 wherein the saturated magnetic field in the ferromagnetic element, the flux leakage in the saturated magnetic field in the ferromagnetic element, and the driven fields induced in the ferromagnetic element by the fluctuating magnetic field are each detected adjacent to and spaced from the periphery of the ferromagnetic element.

13. The method of claim 2 further comprising varying the transverse position of the ferromagnetic element relative to the saturating magnetic field and the fluctuating magnetic field.

14. The method of claim 2 further comprising varying the transverse position of the ferromagnetic element relative to both the saturated magnetic field in the ferromagnetic element and the driven fields induced in the ferromagnetic element by the fluctuating magnetic fields.

15. The method of claim 2 wherein the velocity of the ferromagnetic element relative to the saturating and fluctuating magnetic fields is variable.

16. The method of claim 2 wherein the ferromagnetic element comprises a tubular element.

17. A method of determining the extent of defects in a continuous ferromagnetic tubular string formed of a plurality of interconnected tubular elements, during axial movement of the tubular string, comprising the steps of:

successively applying a saturating magnetic field to each tubular element of sufficient intensity to saturate the portion of the tubular element within the saturating magnetic field during movement of each tubular element therethrough;

detecting the total magnetic flux generated by the saturating magnetic field in each tubular element to detect a wall thickness defect along the length of each tubular element;

detecting a change in flux leakage in the saturated magnetic field to measure the depth of local defects in each tubular element;

applying a cyclic magnetic field to each tubular element in addition to the saturating magnetic field;

detecting driven fields induced in each tubular element by the cyclic magnetic field and comparing the driven fields to the cyclic magnetic field to detect axially extending defects located at discrete circumferential locations on each tubular element;

measuring the velocity of the tubular string by detecting, at a location fixed relative to the saturating magnetic field, a first signal dependent upon the velocity of the tubular string relative to the saturating magnetic field and upon a magnetic field;

detecting a second signal dependent upon the magnetic field and independent of the velocity of the tubular string;

comparing the first signal to the second signal to measure the velocity of the tubular string; and detecting the ends of each tubular element and recording defects as a function of their axial position relative to the end of each tubular element.

18. The method of claim 17 wherein a DC saturating magnetic field induces a longitudinal saturated magnetic field into the tabular element.

19. The method of claim 17 wherein the step of detecting a change in flux leakage to measure the depth of local defects comprises measuring multiple defects having irregular lengths and widths.

20. The method of claim 17 wherein the cyclic magnetic field comprises an AC transverse magnetic field.

21. The method of claim 17 wherein the saturated magnetic field in each tubular element, the flux leakage in the saturated magnetic field in each tubular element, and the driven fields induced in each tubular element by the cyclic magnetic field are each detected adjacent to and spaced from the exterior of the tubular string.

22. The method of claim 17 further comprising varying the transverse position of the tubular string relative to both the saturating magnetic field and the cyclic magnetic field during axial movement thereof.

23. The method of claim 17 wherein the axial velocity of the tubular string is variable.

24. A method of determining the extent of defects in ferromagnetic tubing sections comprising a continuous tubing string used in a subterranean well bore at the well head as the tubing string travels into or out of the well bore, comprising the steps of:
   successively applying a uniform saturating magnetic field along the length of each tubing section of sufficient intensity to saturate the portion of the tubing section within the saturating magnetic field as the tubing string travels axially relative to the well bore;
   detecting the total magnetic flux generated by the saturated magnetic field in each tubing section to detect a wall thickness defect along the length of each tubing section;
   detecting a change in flux leakage in the saturated magnetic field to measure the depth of local corrosion pits on each tubing section;
   applying a cyclic transverse magnetic field to each tubing element in addition to the saturating magnetic field;
   detecting driven fields induced in each tubing section by the cyclic magnetic field and comparing the driven fields to the cyclic magnetic field to detect axially extending defects, including wear defects due to sucker rod interference, located at discrete circumferential locations on each tubular section;
   determining the axial location of measured defects within each tubular section by magnetically detecting the ends of each tubular section; and
   magnetically detecting the velocity of each tubular section.

25. The method of claim 24 further comprising varying the transverse position of the tubular string relative to both the saturating magnetic field and the cyclic magnetic field during axial movement thereof.

26. The method of claim 24 further comprising the step of varying the axial velocity of the tubular string.

27. A tubing trip tool for determining at the well head the extent of defects in ferromagnetic tubing sections of a continuous tubing string used in a subterranean well bore as the tubing string travels into or out of the well bore, comprising:
   means for measuring the axial velocity of each tubular section relative to a saturating magnetic field including means for detecting, at a fixed location within the saturating magnetic field, a first signal produced by the changing magnetic leakage fields emanating from the tubular section due to axial velocity of the tubular section and axial changes in the magnetic properties of the tubing section due to movement of each tubing section, means for detecting a second signal simultaneously produced by the magnetic leakage emanating from the section due to axial changes in the magnetic properties of the tubing section, and means for comparing the first and second signals to measure the velocity of the tubing string;
   means transversely spaced from the tubing string for successively applying a saturating magnetic field along the length of each tubing section of sufficient intensity to saturate the portion of the tubing section within the saturating magnetic field as the tubing string travels axially relative to the wall head;
   means transversely spaced from the tubing string for detecting the total magnetic flux generated by the saturated magnetic field in each tubing section;
   means for correlating the total magnetic flux generated by the saturated magnetic field in each tubing section to the average wall thickness along the length of each tubing section;
   means transversely spaced from the tubing string for detecting flux leakage in the saturated magnetic field of each tubing section;
   means for correlating the flux leakage in the saturated magnetic field of each tubing section to the depth of defects in each tubing section;
   means transversely spaced from the tubing string for applying a cyclic magnetic field to each tubing section in addition to the saturating magnetic field;
   means transversely spaced from the tubing string for detecting driven fields induced in each tubing section by the cyclic magnetic field;
   means for comparing the driven fields to the cyclic magnetic field; and
   means for correlating the difference between the driven fields and the cyclic magnetic fields to the extent of axially extending defects, including wear defects due to sucker rod interference, located at discrete circumferential locations on each tubular section.

28. The tubing trip tool of claim 27 wherein the second signal is responsive to changes in the magnetic flux leakage density of the tubing section and is produced in at least two separate elements within a circuit in which the first signal is produced.

29. The tubing trip tool of claim 28 wherein the separate elements in the circuit comprise elements generating a voltage due to Hall effect.

30. The tubing trip tool of claim 27 wherein the means for applying a saturating magnetic field comprises means for applying a DC magnetic field.

31. The tubing trip tool of claim 27 wherein the means for applying the saturating magnetic field comprises electric coil means encircling the tubing string at the well head.

32. The tubing trip tool of claim 31 wherein the means for detecting the total magnetic field comprises pick up coil means encircling the tubing string and fixed relative to the saturating field.

33. The tubing trip tool of claim 27 wherein the means for correlating the flux leakage in the saturated magnetic field of each tubing section includes means for comparing two non-zero derivatives of different orders of a longitudinal component of the flux leakage in the saturated magnetic field to measure the depth of the defects in each tubing section.

34. The tubing trip tool of claim 33 wherein the means for detecting flux leakage in the saturated magnetic field comprises means for detecting a longitudinal component of the flux leakage in the saturated magnetic field at the maximum value of the flux leakage.

35. The tubing trip tool of claim 34 wherein the means for detecting the longitudinal component of the flux leakage comprise voltage generating elements.

36. The tubing trip tool of claim 35 wherein the voltage generating elements comprise elements in which a voltage is generated by Hall effect and in which the voltage generating elements are oriented transversely to measure the longitudinal component of the flux leakage.

37. The tubing trip tool of claim 33 wherein the means for detecting flux leakage in the saturated magnetic field comprise a plurality of axially spaced elements in which a voltage is generated by Hall effect.

38. The tubing trip tool of claim 27 wherein the means for correlating the flux leakage in the saturated magnetic field to the depth of defects comprises means for correlating the individual depth of multiple defects having irregular lengths and widths.

39. The tubing trip tool of claim 27 wherein the means for detecting flux leakage in the saturated magnetic field is insensitive to the axial velocity of the tubing string.

40. The tubing trip tool of claim 27 wherein the means for detecting the leakage in the saturated magnetic field comprises a plurality of axially spaced voltage generating elements encircling the tubing string to determine the shape of the leakage field.

41. The tubing trip tool of claim 27 wherein the means for applying a cyclic magnetic field comprise means for applying a transverse AC magnetic field.

42. The tubing trip tool of claim 27 wherein the driven fields induced in the tubing sections by the cyclic magnetic field results from eddy current effects and flux leakage of the tubing sections.

43. The tubing trip tool of claim 27 further comprising means for rotating the cyclic magnetic field around each tubing section.

44. The tubing trip tool of claim 43 wherein the means for applying the cyclic magnetic field comprise two coils, and the means for rotating the cyclic magnetic field around each tubing string comprise sinusoidal driving power to electrical conductors in the coils, the sinusoidal driving power to one coil being phase displaced relative to the driving power to the other coil.

45. The tubing trip tool of claim 44 wherein one coil has a sine driving power to the electrical conductors and the other coil has a cosine driving power to the electrical conductors.

46. The tubing trip tool of claim 27 wherein the means for comparing the driven fields to the cyclic magnetic field comprise means for measuring the change in phase between the amplitude of the cyclic magnetic field and the driven fields.

47. Apparatus for determining the extent of defects due to corrosion pitting, sucker rod wear interference, and wall thickness reduction in tubular sections, connectable to form a continuous tubular string used in a subterranean well bore, at the well head as the tubular string travels into or out of the well bore, the apparatus comprising head means locatable at the wellhead surrounding the tubular string and means for processing signals generated in the head means, the head means further comprising:

first drive coil means disposable surrounding the tubular string for successively applying a uniform magnetic field along a portion of each tubular section;

second drive coil means concentrically disposed within the first drive coil means for successively applying a fluctuating magnetic field in addition to the uniform magnetic field along a portion of each tubular section;

a first detecting coil means disposable encircling the tubular string for detecting the total magnetic flux generated in each tubular section by the uniform magnetic field to determine the wall thickness reduction of each tubular section;

a second detecting coil means concentrically disposed within the first detecting coil means and the second drive coil means and disposable encircling the tubular string for detecting driven fields induced in each tubular section by the second drive coil means for determining the extent of sucker rod wear interference defects in each tubular section; and a plurality of detecting elements disposed within the first drive coil means each circumferentially disposable about the tubular string for detecting flux leakage in the total magnetic field induced in each tubular section by the uniform magnetic field to determine the depth of corrosion pitting defects in each tubular section.

48. The apparatus of claim 47 wherein the plurality of detecting elements are disposed at a plurality of circumferential locations within the first detecting coil means and at least some of the plurality of detecting elements are axially spaced from other of the plurality of elements.

49. The apparatus of claim 47 wherein the second detecting coil means comprises detecting coil conductors disposed to define an annular volume surrounded by radially spaced, axially extending detecting coil conductor sections and axially spaced, radially extending detecting coil conductor sections, whereby a plane through end conductor sections of a respective coil conductor defines corresponding coil planes transverse to field lines of the driven fields induced in the tubular sections by the second drive coil means.

50. The apparatus of claim 49 wherein the plurality of detecting elements are disposed at a plurality of circumferential locations within the annular volume defined by the detecting coil conductors comprising the second detecting coil means and at least some of the plurality of detecting elements are axially spaced from other of the plurality of elements.

51. The apparatus of claim 50 wherein the axially spaced detecting elements comprise elements for generating an electrical current in response to Hall effect.

52. The apparatus of claim 47 wherein a portion of the detection head means is expandable, the expandable portion comprising a plurality of arcuate segments each including portions of the second drive coil means, portions of the second detecting coil means, and at least some of the detecting elements.

53. The apparatus of claim 47 wherein the second drive coil means, the second detecting coil means and the detecting elements are separately encapsulated within an electrically insulating material.

54. A method of claim 1, further comprising the steps of:

measuring the velocity of the ferromagnetic elements by detecting, at a location fixed relative to the saturating magnetic field, a first signal dependent upon the velocity of the ferromagnetic element relative to the saturating magnetic field and upon a magnetic field;

detecting a second signal dependent upon the magnetic field and independent of the velocity of the element; and comparing the first signal to the second signal to measure the velocity of the ferromagnetic element.

55. The method of claim 1, wherein the depth of defects is determined by signal processing employing a plurality of detectors selectively spaced geometrically relative to the ferromagnetic element to detect the change in flux leakage.

56. Apparatus for detecting defects in ferromagnetic tubular elements during axial movement of the tubular elements, comprising:
   means spaced from the tubular elements for applying a saturating magnetic field along the length of a tubing element of sufficient intensity to saturate a portion of the tubing section within the saturating magnetic field as the tubing element travels axially relative to the saturating magnetic field;
   means transversely spaced from the tubing elements for detecting the total magnetic flux generated by the saturated magnetic field;
   means for correlating the total magnetic flux generated by the saturating magnetic field to detect a wall thickness defect along the length of each tubing section;
   means transversely spaced from the tubing string for detecting flux leakage in the saturated magnetic field of each tubing string;
   means for comparing two non-zero derivatives of different orders of a longitudinal component of the flux leakage in the saturated magnetic field as altered by the defects to determine the depth of defects in each tubing section; and
   means for detecting the extent of axially extending defects in each tubing section.

57. The apparatus of claim 56 wherein said means for detecting axially extended defects comprises:
   means transversely spaced from the tubing string for applying a cyclic magnetic field to each tubing string in addition to the saturating magnetic field;
   means transversely spaced from the tubing string for detecting the driven fields induced in each tubing string by the cyclic magnetic field;
   means for comparing the driven fields to the cyclic magnetic field; and
   means for correlating the difference between the driven fields and the cyclic magnetic fields to the extent of axially extending defects located at circumferential locations on each tubular section.

58. A method of determining the extent of defects in a ferromagnetic element during axial movement of the ferromagnetic element, comprising the steps of:
   applying a saturating magnetic field to the ferromagnetic element of a sufficient intensity to produce a saturated magnetic field in the portion of the ferromagnetic element passing through the magnetic saturating field;
   detecting a change in the total magnetic flux generated by the saturated magnetic field in the ferromagnetic element to detect a cross-sectional area defect in the ferromagnetic element;
   detecting a change in flux leakage in the saturated magnetic field to measure the depth of local defects in the ferromagnetic element;
   applying a fluctuating magnetic field to the ferromagnetic element in addition to the saturating magnetic field;
   measuring the velocity of the ferromagnetic element by detecting, at a location fixed relative to the saturating magnetic field, a first signal dependent upon the velocity of the element relative to the saturating magnetic field and upon a magnetic leakage field;
   detecting a second signal dependent upon the magnetic leakage field and independent of the velocity of the element;
   comparing the first signal to the second signal to measure the velocity of the ferromagnetic element;
   detecting driven fields induced in the ferromagnetic element by the fluctuating magnetic field and comparing the driven fields to the fluctuating magnetic field to detect axially extending defects located at discrete lateral locations relative to the axis of and in the ferromagnetic element; and
   recording defects as a function of their axial position in the ferromagnetic element.

59. The method of claim 58 wherein the saturating magnetic field induces a saturation value of magnetic flux extending axially in the portion of the ferromagnetic element extending through the saturating magnetic field.

60. The method of claim 58 wherein the depth of local defects is determined by signal processing employing a plurality of detectors selectively spaced geometrically relative to the ferromagnetic element to detect the change in flux leakage.

61. The method of claim 58 wherein the step of detecting a change in flux leakage to measure the depth of local defects comprises positioning a plurality of axially spaced voltage generating flux leakage detection elements around the ferromagnetic element to determine the shape of the leakage field.

62. The method of claim 58 further comprising varying the longitudinal position of the ferromagnetic element relative to both the saturated magnetic field in the ferromagnetic element and the driven fields induced in the ferromagnetic element by the fluctuating magnetic fields.

63. The method of claim 2, wherein the derivatives of the axial component of flux leakage are compared at a maximum value of flux leakage.

64. Apparatus for determining at the well head the extent of defects due to radially-extending defects, axially-extending defects, and wall thickness defects in tubular sections of a tubular string used in a subterranean well bore as the tubular string travels into or out of the well bore, the apparatus comprising:
   first drive coil means disposable in surrounding relationship with respect to the tubular string at the well head for successively applying a uniform magnetic field along a portion of each tubular section;
   second drive coil means concentrically disposed within the first drive coil means for successively applying a fluctuating magnetic field in addition to the uniform magnetic field along a portion of each tubular section;
   a first detecting coil means disposable in encircling relationship with respect to the tubular string for detecting the total magnetic flux generated in each tubular section by the uniform magnetic field to determine the wall thickness defects in each tubular section;
   a second detecting coil means concentrically disposed within the first detecting coil means and the second drive coil means and disposable in encircling relationship with respect to the tubular string for detecting driven fields induced in each tubular section by the second drive coil means for determining the extent of the axially-extending defects in each tubular section;

a plurality of detecting elements disposed within the first drive coil means each circumferentially disposable about the tubular string for detecting flux leakage in the total magnetic field induced in each tubular section by the uniform magnetic field to determine the depth of the radially-extending defects in each tubular section; and means for processing signals from the first detecting coil means, the second detecting coil means, and the plurality of detecting elements.

65. The apparatus of claim 64 wherein the plurality of detecting elements are disposed at a plurality of circumferential locations within the first detecting coil means and at least some of said plurality of detecting elements are axially spaced from other of said plurality of elements.

66. The apparatus of claim 64 wherein the second detecting coil means comprises detecting coil conductors disposed to define an annular volume surrounded by radially spaced, axially extending detecting coil conductor sections and axially spaced, radially extending detecting coil conductor sections, whereby a plane through end conductor sections of a respective coil conductor defines corresponding coil planes transverse to field lines of the driven fields induced in the tubular sections by the second drive coil means.

67. The apparatus of claim 64 wherein the plurality of detecting elements are disposed at a plurality of circumferential locations within the annular volume defined by the detecting coil conductors comprising the second detecting coil means and at least some of the plurality of detecting elements are axially spaced from other of the plurality of elements.

* * * * *